United States Patent
Palmaz

(10) Patent No.: US 8,617,238 B2
(45) Date of Patent: Dec. 31, 2013

(54) TRANSLUMINAL CARDIAC BALL VALVE AND METHOD FOR DEPLOYMENT THEREOF

(75) Inventor: Julio C. Palmaz, Napa, CA (US)

(73) Assignee: Palmaz Scientific, Inc., Dallas, TX (US)

( * ) Notice: Subject to any disclaimer, the term of this patent is extended or adjusted under 35 U.S.C. 154(b) by 0 days.

(21) Appl. No.: 13/468,667

(22) Filed: May 10, 2012

(65) Prior Publication Data

US 2012/0239141 A1  Sep. 20, 2012

Related U.S. Application Data

(63) Continuation of application No. PCT/US2011/048121, filed on Aug. 17, 2011.

(60) Provisional application No. 61/374,558, filed on Aug. 17, 2010, provisional application No. 61/380,093, filed on Sep. 3, 2010.

(51) Int. Cl.
*A61F 2/24* (2006.01)

(52) U.S. Cl.
USPC .......................................................... 623/2.35

(58) Field of Classification Search
CPC .... A61F 2/2421; A61F 2/2424; A61F 2/2475
USPC ................................................ 623/2.34, 2.35
See application file for complete search history.

(56) References Cited

U.S. PATENT DOCUMENTS

| | | | |
|---|---|---|---|
| 5,232,445 A | 8/1993 | Bonzel | 604/96 |
| 5,387,247 A | 2/1995 | Vallana et al. | 623/66 |
| 5,397,351 A * | 3/1995 | Pavcnik et al. | 623/2.35 |
| 5,607,463 A | 3/1997 | Schwartz et al. | 623/1 |
| 5,626,600 A | 5/1997 | Horzewski et al. | 606/194 |
| 5,649,951 A | 7/1997 | Davidson | 606/198 |
| 5,690,670 A | 11/1997 | Davidson | 606/198 |
| 5,725,573 A | 3/1998 | Dearnaley et al. | 623/2 |
| 5,782,908 A | 7/1998 | Cahalan et al. | 623/1 |
| 5,891,507 A | 4/1999 | Jayaraman | 427/2.25 |
| 5,897,911 A | 4/1999 | Loeffler | 427/2.25 |
| 5,932,299 A | 8/1999 | Katoot | 427/508 |
| 5,955,588 A | 9/1999 | Tsang et al. | 536/21 |
| 6,936,066 B2 | 8/2005 | Palmaz et al. | 623/1.13 |
| 2002/0032481 A1 | 3/2002 | Gabbay | 623/2.11 |

(Continued)

FOREIGN PATENT DOCUMENTS

WO  WO 03/003943  1/2003

OTHER PUBLICATIONS

Davies, P.F., et al., "Endothelial cell adhesion in real time" *J Clin Invest* 91: 2640-2652 (1993).
Davies, P.F., et al., "Qualitiative studies of endothelial cell adhesion" *J Clin Invest* 93: 2031-2038 (1994).

(Continued)

*Primary Examiner* — Thomas J Sweet
*Assistant Examiner* — Megan Wolf
(74) *Attorney, Agent, or Firm* — J. Peter Paredes; Rosenbaum IP

(57) ABSTRACT

A transluminal cardiac valve includes an expandable generally tubular cage including when expanded a generally uniform central region, first and second ends each diametrically constricted relative to the central region, a blood impervious region extending from the first end of the cage to within the generally uniform central region, and an inflatable plunger freely disposed and captured within the cage when inflated.

20 Claims, 15 Drawing Sheets

(56) References Cited

U.S. PATENT DOCUMENTS

| | | | |
|---|---|---|---|
| 2004/0034411 A1 | 2/2004 | Quijano et al. | 623/2.11 |
| 2006/0287719 A1* | 12/2006 | Rowe et al. | 623/2.18 |
| 2007/0078509 A1* | 4/2007 | Lotfy | 623/1.24 |
| 2009/0248149 A1 | 10/2009 | Gabbay | 623/2.37 |

OTHER PUBLICATIONS

Holleck, H., et al., "Multilayer PVD coatings for wear protection" *Surface and Coatings Technology* 76-77: 328-336 (1995).

Vroman L., "The importance of surfaces in contact phase reactions" *Seminars of Thrombosis and Hemostasis* 13(1): 79-85 (1987).

* cited by examiner

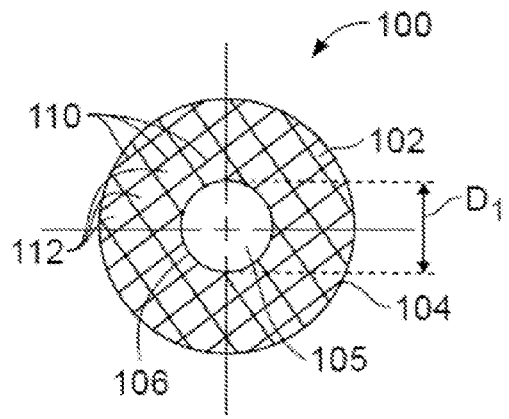
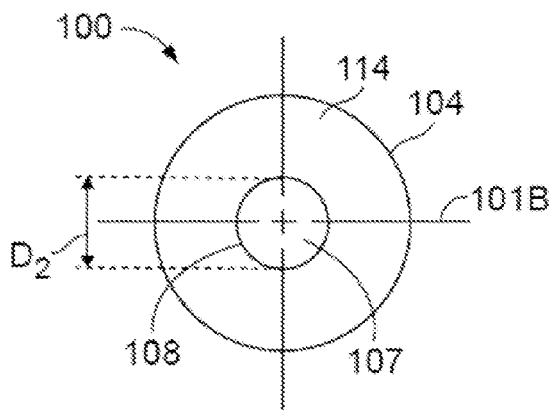
FIG. 3     FIG. 4
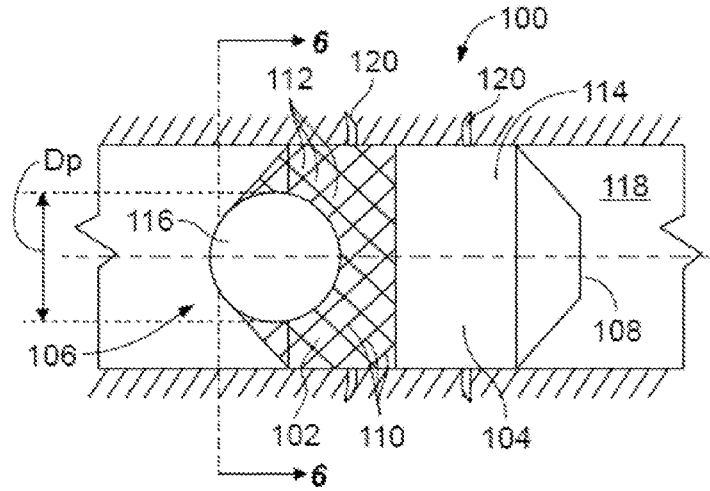
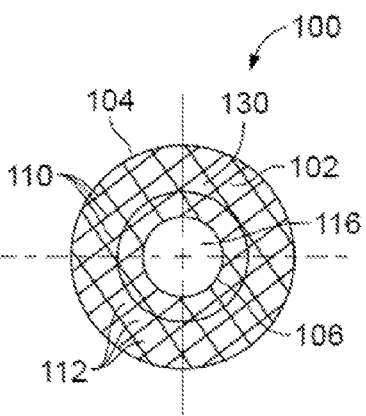
FIG. 5     FIG. 6
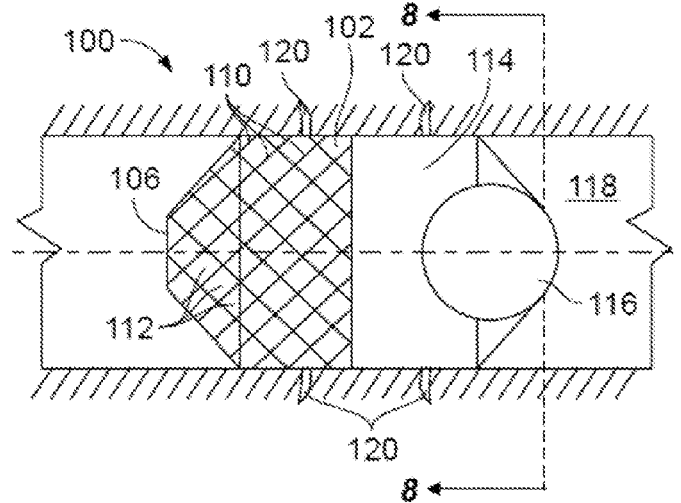
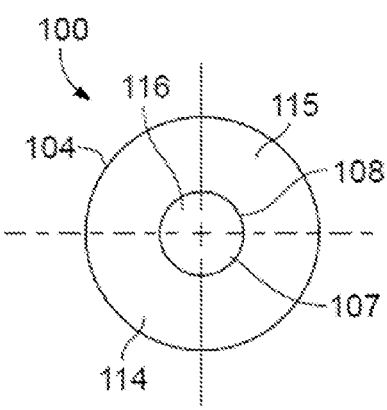
FIG. 7     FIG. 8

TRANSLUMINAL CARDIAC BALL VALVE AND METHOD FOR DEPLOYMENT THEREOF

CROSS-REFERENCE TO RELATED APPLICATIONS

The present application is a continuation of PCT Application Serial No. PCT/US2011/048121, filed Aug. 17, 2011, which claims priority to U.S. Provisional Application Ser. No. 61/374,558, filed Aug. 17, 2010, and claims priority to U.S. Provisional Application Ser. No. 61/380,093, filed Sep. 3, 2010, all incorporated by reference in their entirety herewith.

BACKGROUND OF THE INVENTION

The present invention relates generally to a cardiac valve suitable for implantation into mammalian subjects in need thereof. More particularly, the present invention pertains to a prosthetic transluminal plunger and cage cardiac valve that employs such plunger free to reciprocally move within a transluminal cage member under the influence of pressure differentials due to systole and diastole. It is desirable, although not essential to the present invention, that the prosthetic cardiac valve be capable of being delivered using endovascular techniques and being implanted at an intracardiac, intra-arterial, or intravenous site without the need for anatomic valve removal. Placement of the valve can be at an anatomical site of a damaged valve or in the descending thoracic aorta, depending on the tolerance of the patient. The former can be accessed through a trans-arterial or transcardiac approach; the latter through upper or lower extremity arterial access.

The prior art discloses percutaneously delivered prosthetic ball and cage valves. One such valve is made of shape memory nitinol and consists of a stent and a flow regulation mechanism. The stent comprises a meshwork or braiding of nitinol wire with trumpet like distal and proximal flares. The purpose of the stent is to maintain a semi-ridged patent channel through a diseased cardiac valve after initial balloon dilation. The flared ends are intended to maintain the position of the stent component across the valve thereby anchoring the vascular device. The flow-regulation mechanism includes a caged ball delivered secondary to the stent, thus requiring two catheters for delivery in addition to any initial valvuloplasty, which increases the time, costs, risks, difficulty and trauma associated with a percutaneous procedure. Due to the flared ends, this valve may be problematic for implantation in a patient's descending aorta. Further, the tines of the ball cage may prevent a solid continuous contact with the braided stent therefore allowing for leakage. Also, the portion of the ball cage where the tines come together with the anchor funnel would be obstructive to the flow, leading to thrombosis.

Another such valve comprises a cage mechanism comprised of a multiplicity of crisscrossed wires connected to a self-expanding stent and a seal ring connected thereto via a single stainless steel rod. A first catheter is used for implantation of the seal ring, cage, and stent, which is disposed between the ring and a cage mechanism. A second catheter is required for implantation of the balloon, which seals against the ring and allows fluid flow through the cage. Because opposite ends of the valve are connected only by the single rod, the valve may be problematic with regard to longitudinal stability.

A need exists for an improved transluminal valve of size and configuration such that the improved valve is implantable via a single catheter sheath. The improved valve would benefit from having a sturdy and durable construction with uniform geometry inherently afforded by a plunger and cage valve comprising a monolithic cage and a plunger both potentially made from multiple vacuum deposited material layers. Coverage of a portion of the monolithic cage with endothelial cells may be enhanced by depositing controlled heterogeneities along the portion of the cage. Further, patients needing transluminal valves are typically older, debilitated, and unlikely to tolerate major surgery and a significant portion of the morbidity and mortality associated with current transluminal valve placement is related to the large diameter and low flexibility of the introducer systems. Thus, the improved cardiac valve would further benefit from being sized to fit a 12-14 F introducer, thereby reducing the potential for stroke, hemorrhage, lower extremity ischemia, and other serious complications. The present invention solves these problems, as well as others.

SUMMARY OF THE INVENTION

In a first embodiment, a transluminal cardiac valve includes an expandable generally tubular cage including when expanded a generally uniform central region, first and second ends each diametrically constricted relative to the central region, and a blood impervious region extending from the first end of the cage to within the generally uniform central region. The valve further includes an inflatable plunger inflated to have a shape generally resembling a ball, cylinder, or disk and freely disposed and captured within the cage when inflated.

In another embodiment, a transluminal cardiac valve includes an operational state including a generally tubular cage disposed in an expanded configuration having a generally uniform central region, first and second ends each diametrically constricted relative to the central region, and a blood impervious region extending from the first end of the cage to within the generally uniform central region. The operational state further includes an inflatable plunger inflated to have a shape generally resembling a ball, cylinder, or disk and freely disposed and captured within the cage when inflated. The valve further includes a delivery state including the generally tubular cage disposed in a collapsed configuration and crimped onto an inflation balloon that is attached to and in fluid communication with an inflation catheter.

In a further embodiment, a method for delivery of a transluminal cardiac valve includes the steps described hereinbelow. The cardiac valve includes an operational state comprising a generally tubular cage disposed in an expanded configuration having a generally uniform central region, first and second ends each diametrically constricted relative to the central region, and a blood impervious region extending from the first end of the cage to within the generally uniform central region. The cage can be made of a martensitic alloy and be deployed by a coaxial balloon or can be self-expanding. The latter would require an austenitic alloy construction and post deployment balloon dilatation to achieve adequate setting of the cage at the site of implantation.

The operational state further includes an inflatable plunger freely disposed and captured within the cage when inflated. The valve further includes a delivery state including the generally tubular cage disposed in a collapsed configuration and crimped onto an inflation balloon that is attached to and in fluid communication with a first inflation catheter, and the inflatable plunger deflated and in fluid communication with a second inflation catheter.

The method for deployment includes the steps of inserting the generally tubular cage in the delivery state into a lumen of a catheter sheath such that the cage is disposed proximate a distal end of the catheter sheath and advancing the catheter sheath into a patient until the cage is disposed at an implantation site. A further step in the method is translating the catheter sheath proximally relative to the first inflation catheter until the cage is free from being contained within the lumen. After ideal position is confirmed by fluoroscopy and transesophageal echocardiography, the heart will be rapid paced to minimize motion and the cage will be deployed by inflating the inflation balloon to expand the cage. Further steps include deflating the inflation balloon, removing the thus deflated inflation balloon and the first inflation catheter from the lumen, and inserting the inflatable plunger in the delivery state such that the inflatable plunger is disposed within the cage. Yet further steps in the method include inflating the inflatable plunger to the expanded configuration with fluid via the second inflation catheter, detaching the second inflation catheter from the inflatable plunger thus inflated to the expanded configuration, and removing the second inflation catheter and the catheter sheath from the patient.

BRIEF DESCRIPTION OF THE FIGURES

FIG. 3 is a cross-sectional view taken generally along line 3-3 of FIG. 2.

FIG. 4 is a cross-sectional view taken generally along line 4-4 of FIG. 2.

FIG. 5 is a cross-sectional view of the valve of FIG. 1 implanted at an implantation site taken generally along line 2-2 of FIG. 1.

FIG. 6 is an end-on view taken generally along line 6-6 of FIG. 5.

FIG. 7 is another cross-sectional view of the valve of FIG. 1 implanted at an implantation site taken generally along line 2-2 of FIG. 1.

FIG. 8 is an end-on view taken generally along line 8-8 of FIG. 7.

DETAILED DESCRIPTION OF THE PREFERRED EMBODIMENTS

An orientational definition is provided with respect to a catheter sheath or inflation catheter as described herein, the term "proximal" is intended to mean toward the operator end of the catheter, while the term "distal" is intended to mean toward the terminal end or device-carrying end of the catheter. For purposes of this application, the term "pseudometal" or "pseudometallic" is intended to mean a biocompatible material which exhibits biological response and material characteristics substantially the same as biocompatible metals, such as for example composite materials.

In accordance with one embodiment, the plunger and/or the cage member may be made of a single material, such as stainless steel, nickel titanium alloy, cobalt-chromium alloy, or other biocompatible materials suitable for manufacture of valvular prosthetics. In accordance with an alternative embodiment, the plunger and/or the cage member may be made of at least two layers formed upon one another into a self-supporting laminate structure.

In order to improve healing response, the materials employed have substantially homogenous surface profiles at the blood or tissue contact surfaces thereof. A substantially homogeneous surface profile is achieved by controlling heterogeneities along the blood or tissue-contacting surface of the material. The heterogeneities that are controlled in accordance with an embodiment include: grain size, grain phase, grain material composition, stent-material composition, and surface topography at the blood flow surface of the stent. Additionally, the embodiments disclosed herein provide methods of making endoluminal devices having controlled heterogeneities in the device material along the blood flow or tissue-contacting surface of the device. Material heterogeneities are preferably controlled by using conventional methods of vacuum deposition of materials onto a substrate.

The surface of a solid, homogeneous material can be conceptualized as having unsaturated inter-atomic and intermolecular bonds forming a reactive plane ready to interact with the environment. In practice, a perfectly clean surface is unattainable because of immediate adsorption of airborne species, upon exposure to ambient air, of O, $O_2$, $CO_2$, $SO_2$, NO, hydrocarbons and other more complex reactive molecules. Reaction with oxygen implies the formation of oxides on a metal surface, a self-limiting process, known as passivation. An oxidized surface is also reactive with air, by adsorbing simple, organic airborne compounds. Assuming the existence of bulk material of homogeneous subsurface and surface composition, oxygen and hydrocarbons may adsorb homogeneously. Therefore, further exposure to another environment, such as the vascular compartment, may be followed by a uniform biological response.

Figure 1:
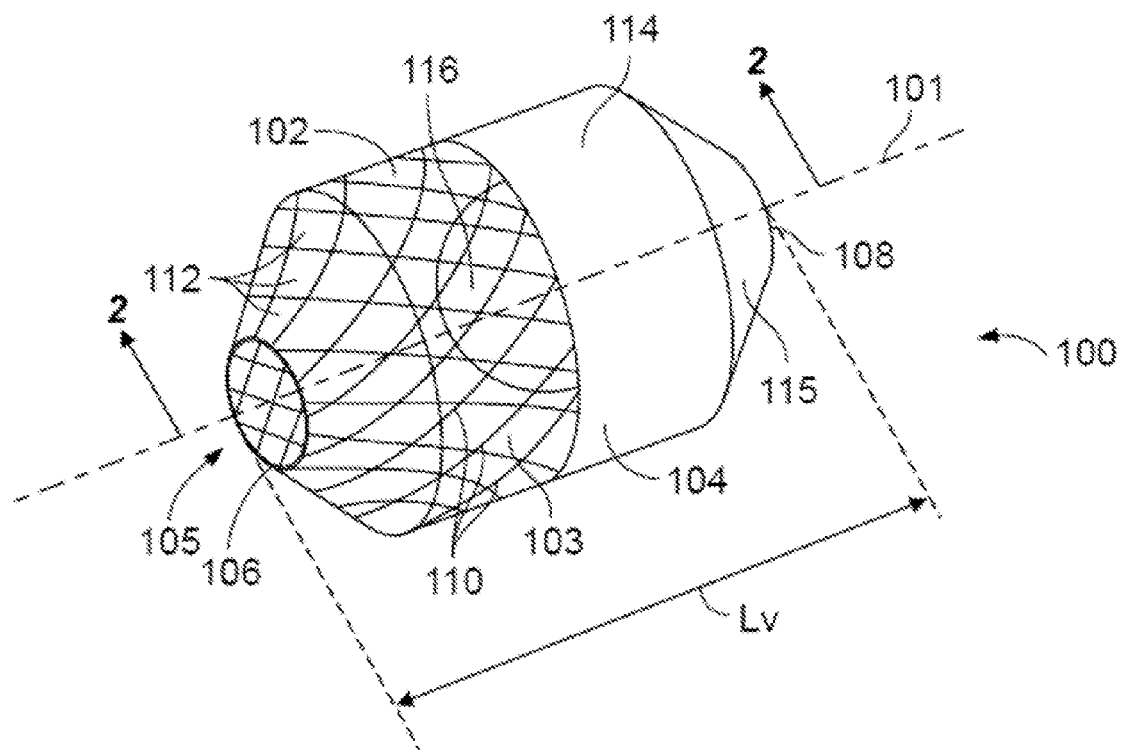
FIG. 1 is a perspective view of an embodiment of a transluminal cardiac valve.

Generally speaking, an embodiment of a transluminal cardiac valve 100 includes a generally tubular cage 102, a blood impervious region 114, a central lumen 103 disposed within the cage 102 and the blood impervious region 114, and an inflatable plunger 116 translatable within the central lumen 103, as illustrated in FIGS. 1-4. The cage 102 and the blood impervious region 114 include a generally uniform central region 104 disposed between a first end 106 and a second end 108, whereby the first end 106 is generally along the proximal end of the valve 100 and the second end 108 is generally along the distal end of the valve 100. The cardiac valve 100 includes a length Lv extending from the first and second ends 106, 108 and along a longitudinal axis 101 of the valve 100. The first and second ends 106, 108 are diametrically constricted relative to the central region 104. The first end 106 includes a first opening 105 and the second end includes a second opening 107, whereby both the first and second openings 105 and 107 are in fluid communication with the lumen 103, as best seen in FIG. 1.

Figure 2:
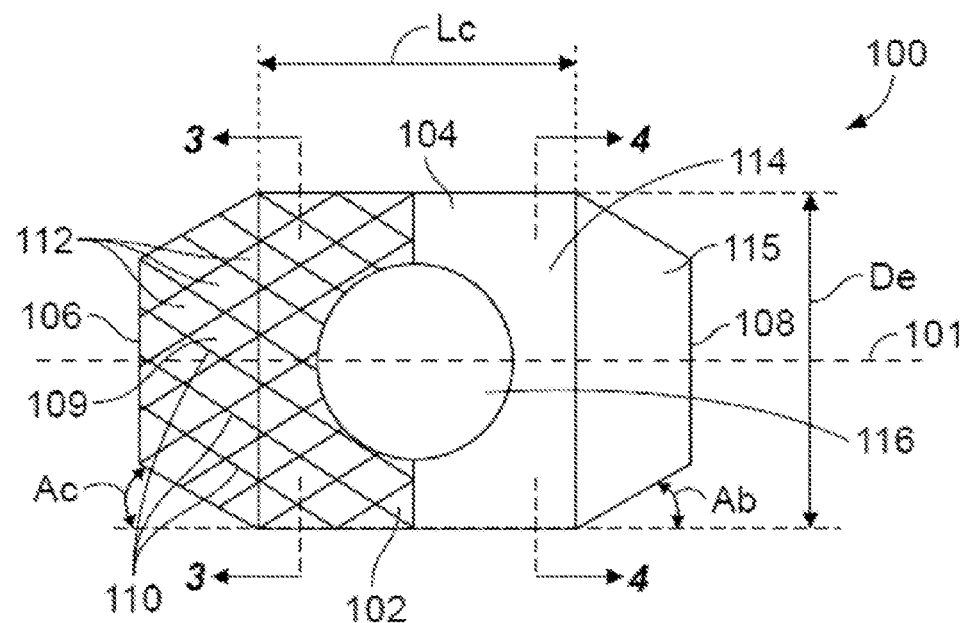
FIG. 2 is a cross-sectional view taken generally along line 2-2 of FIG. 1.

The valve 100 includes a contracted delivery configuration and an expanded operational configuration. When the valve 100 is in the operational state, the cage 102 has an expanded configuration, as illustrated in FIGS. 1-8 and the contracted delivery configuration is illustrated in FIGS. 10, 15-16, 18, and 21-22. The cage 102 is generally stent-like and comprises a plurality of struts 110 forming expanded cells 112 therebetween when the cage 102 is in the expanded configuration. The plurality of struts 110 form contracted cells when in the contracted delivery configuration. The plurality of struts 110 forms a part of the central region 104 and generally forms a cylindrical outer surface that is substantially parallel to the longitudinal axis 101 of the valve 100. Alternatively, the plurality of struts 110 forms a cylindrical outer surface that is substantially non-parallel to the longitudinal axis 101 of the valve. The cage 102 extends about half way along a longitudinal length Lc of the central region 104, as shown in FIG. 2. In other embodiments, the cage 102 may extend less than half way or more than half way along a longitudinal length Lc of the central region 104, for example, entirely across the longitudinal length Lc of the central region 104, or only slightly into the longitudinal length Lc of the central region 104. The distal portion of the cage 102 extends from the proximal portion of the blood impervious region 114. The cage 102 includes a proximal portion 109 that is a generally frustoconical shape that tapers towards to the longitudinal axis 101 from the central region 104. Alternatively, the proximal portion 109 may have other geometric configurations, such as rounded or dome-like configuration, a box or flange-like configuration, or such other configuration as will define a narrowed first end 106 of the cage 102. In one embodiment, the proximal portion 109 includes smaller struts than the struts 110 of the cage 102 contained within the central region 104. In one embodiment, the cage 102 includes a proximal portion 109 that tapers proximally relative to the longitudinal axis at an angle Ac, as shown in FIG. 2. The angle Ac for the proximal tapering of the proximal portion 109 may be between about 10 and 90 degrees, alternatively, between about 20 and 80 degrees, alternatively, between about 30 and 70 degrees, alternatively, between about 40 and 60 degrees. The angle Ac may be selected according to the implantation site 118 selected for the cardiac valve, alternatively, the angle Ac is selected as to bias the inflatable plunger 116 towards the first opening 105 when the inflatable plunger 116 translates towards the proximal end 106, such as at least 45 degrees.

Figure 10:
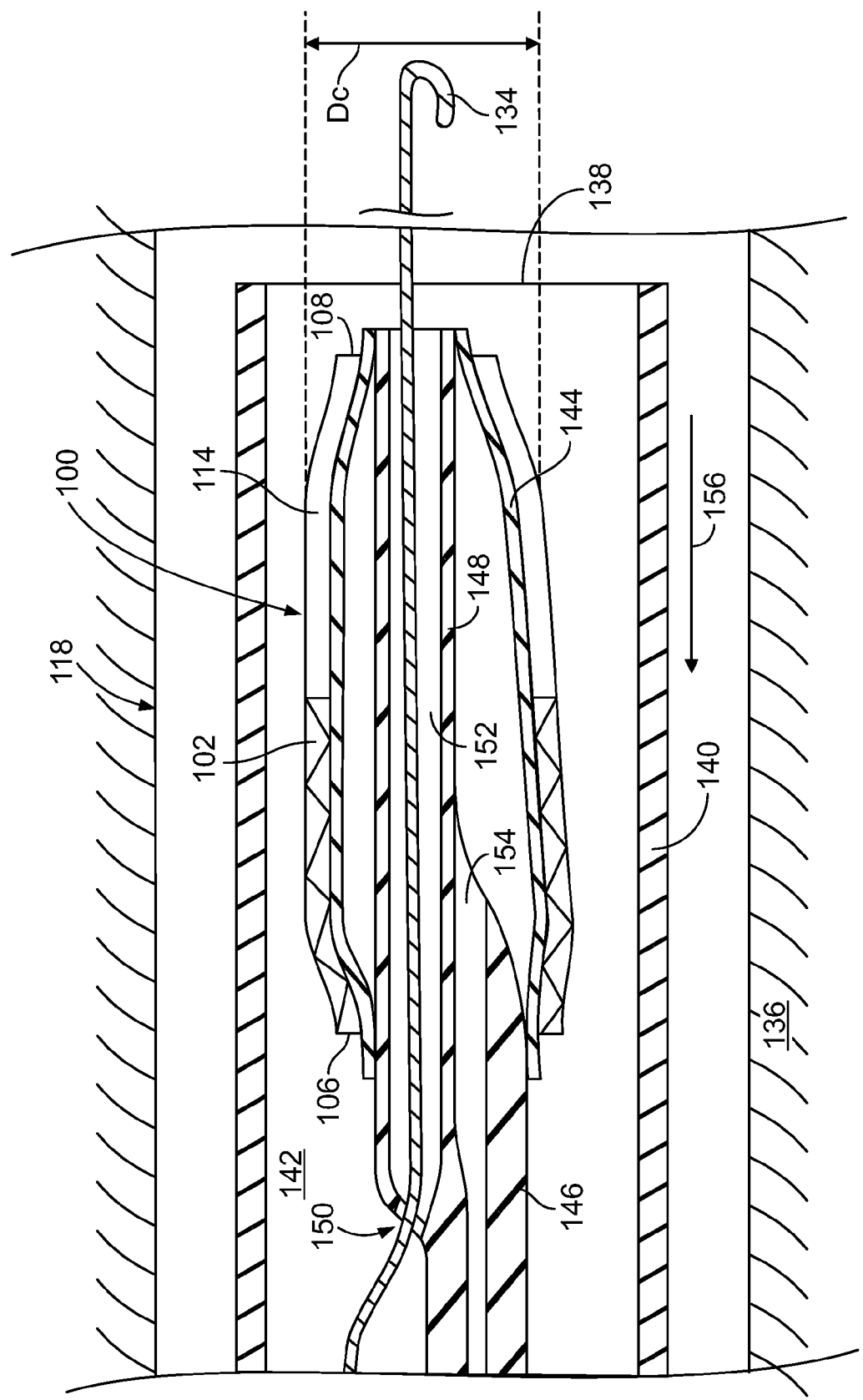
FIG. 10 is a cross-sectional view of an embodiment of a cage of the valve of FIG. 1 in a delivery state loaded into a catheter sheath.
Figure 11:
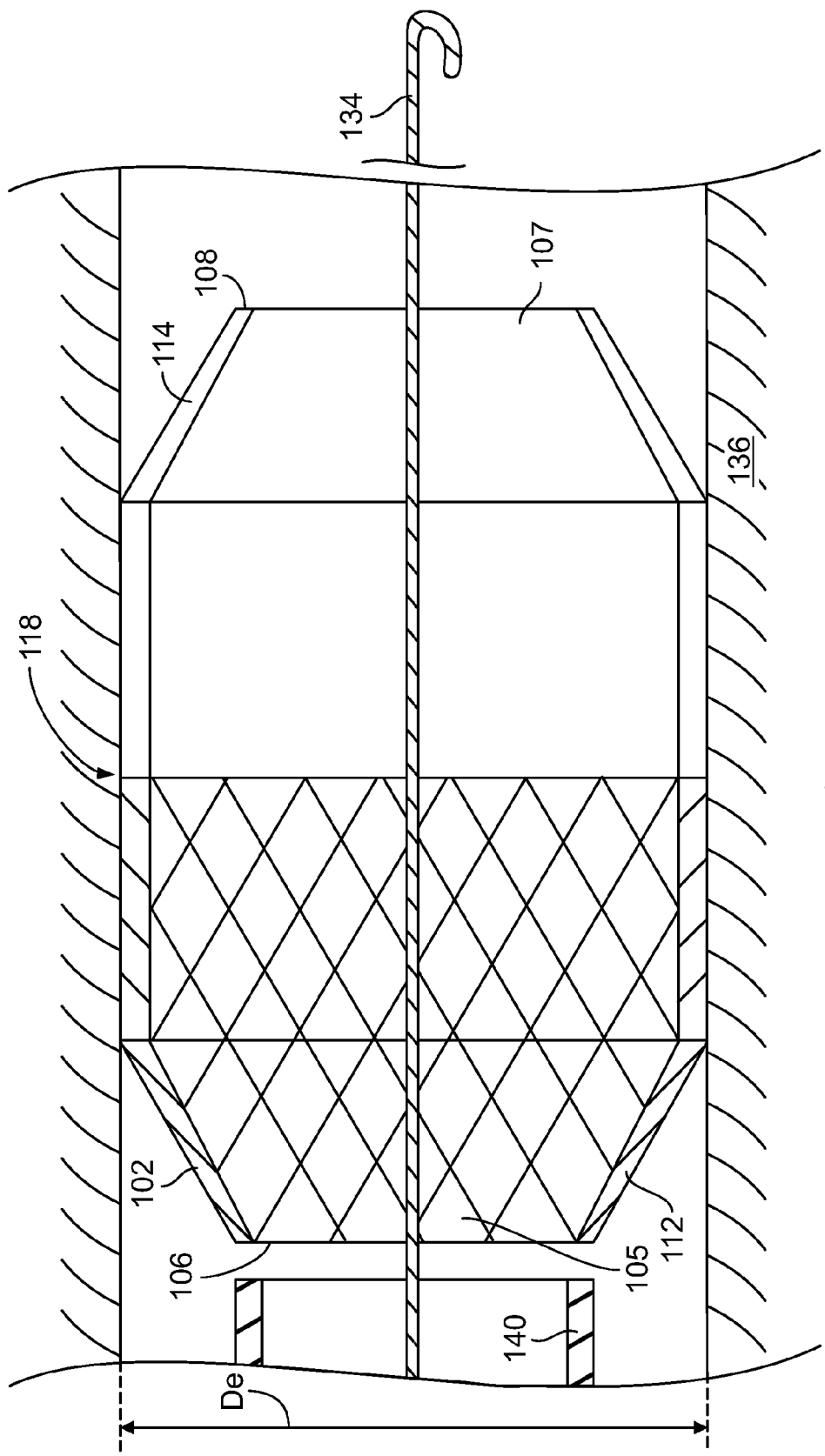
FIG. 11 is a cross-sectional view of the cage of FIG. 10 in an expanded configuration at an implantation site.

In one embodiment, the cage 102 is self-expanding from a collapsed configuration while being contained within a lumen of a catheter sheath to the expanded configuration upon release from the catheter sheath (See FIGS. 10-11). In another embodiment, the cage 102 is balloon expandable (See FIGS. 10-11). The expanded configuration includes a diameter De (see FIG. 2) and the collapsed configuration includes a diameter Dc (see FIG. 10), whereby the diameter De is greater than the diameter Dc. Diameter De may be selected according to the implantation site 118 and adjusted to securely fit the implantation site, while diameter Dc may be selected according to the delivery catheter, as further detailed below. In one embodiment, diameter Dc is between about 2 and 6 mm or 10-16 F, as to fit a 12-14 F introducer, thereby reducing the potential for stroke, hemorrhage, lower extremity ischemia, and other serious complications.

The blood impervious region 114 extends from a distal end of the cage 102 within the generally uniform central region 104 to the second end 108, as illustrated in FIGS. 1, 2, 5, and 7. In this embodiment, the blood impervious region 114 extends about half way along a longitudinal length Lc of the central region 104. In other embodiments, the blood impervious region 114 may extend less than half way or more than half way along a longitudinal length Lc of the central region 104, for example, entirely across the longitudinal length Lc of the central region 104, or only slightly into the longitudinal length Lc of the central region 104. Furthermore, blood impervious region 114 may be configured as a generally frustoconical shape that tapers distally relative to the axis of blood flow through the cage 102. Alternatively, the blood impervious region 114 may have other geometric configurations, such as rounded or dome-like configuration, a box or flange-like configuration, or such other configuration as will define a narrowed second end 108 of the blood impervious region 114. Alternatively, the blood impervious region 114 may include a distal portion 115 that is a generally frustoconical shape that tapers towards to the longitudinal axis 101 from the central region 401. Alternatively, the distal portion 115 may have other geometric configurations, such as rounded or dome-like configuration, a box or flange-like configurations, or such other configuration as will define a narrowed second end 108 of the blood impervious region 114. In one embodiment, the blood impervious region 114 includes a distal portion 115 that tapers distally towards the longitudinal axis 101 at an angle Ab, as shown in FIG. 2. The angle Ab for the distal tapering of the distal portion 115 may be between about 10 and 90 degrees, alternatively, between about 20 and 80 degrees, alternatively, between about 30 and 70 degrees, alternatively, between about 40 and 60 degrees. The angle Ab may be selected according to the implantation site 118 selected for the cardiac valve 100, alternatively, the angle Ab is selected as to bias the inflatable plunger 116 towards the second opening 107 when the inflatable plunger 116 translates towards the distal end 108, such as at least 45 degrees.

The blood impervious region 114 includes a blood impervious material, including by way of example and not limitation, an expandable polymeric material such as porous expanded polytetrafluoroethylene (ePTFE), woven metal mesh or a non-woven porous metal film. If a woven metal mesh is used, then the interstices or cells of the woven metal mesh are filled with a blood impervious material or sized as to not permit blood or other fluids to diffuse therethrough. An example of a non-woven metal film suitable is disclosed in commonly owned U.S. Pat. No. 6,936,066 issued Aug. 30, 2005, which is hereby incorporated by reference. The blood impervious material preferably has a thickness less than the thickness of the struts 110 of the cage 102 and more preferably has a thickness between about 0.1 micrometer and 75 micrometers, and more preferably has a thickness between about 2 micrometers and 25 micrometers. The blood impervious region 114 and material may be manufactured integrally with the cage 102 or may be joined to or otherwise associated with the struts 110 to subtend, cover or occlude the cells 112 in the blood impervious region 114.

The term "blood impervious" is intended to mean the property of preventing blood flow through the material under typical physiological systolic and diastolic pressures (between 90-119 mmHg and 60-79 mmHg), while still permitting cellular migration through the blood impervious material. The blood impervious material may also prevent blood flow through the material at higher or lower systolic and diastolic pressures, such as between 60-180 mmHg. The blood impervious material is intended to provide a lattice for tissue embedment such that the blood impervious region becomes endothelialized and therefore non-thrombogenic. Blood flow through the interstices of the blood impervious material will be minimized prior to the establishment of tissue embedment by using very small openings or by obliterating such openings with a bioabsorbable polymer such as PLA, PCLA, PLLA, etc. Diffusion is also minimized by the endothelialization of the blood impervious material.

The inflatable plunger 116 is longitudinally translatable within the central lumen 103 and along the longitudinal axis 101. The inflatable plunger 116 may be, for example, a generally ball-shaped inflatable plunger, as illustrated in FIGS. 1, 2, and 5-8. When the valve 100 is in the operational state, the inflatable plunger 116 has an expanded configuration, as illustrated in FIGS. 1, 2, and 5-8, and is freely disposed and captured within the cage 102 when longitudinally translated towards the first end 106 and disposed within the first opening 105. The inflatable plunger 116 may be generally spherical including some non-spherical eccentricity, or it may be cylindrical with flat, spherical or conical ends or combinations thereof. Alternatively, the cylinder may be much wider than it is long, therefore having a disk shape. Also, the side surfaces of the inflatable plunger 116 may not conform to a cylinder as they may be convex or concave or combinations thereof. Preferably, the inflatable plunger 116 is selected as to be freely translatable, either along the longitudinal axis 101 or the traverse axis 101b (see FIG. 4), within the central lumen 103 and captured or maintained by the first and second ends 106, 108 within the first and second openings 105, 107, respectively. In this regard, the inflatable plunger 116 includes a diameter Dp once in the expanded or inflated condition (see FIG. 5). The first opening 105 includes a diameter D1, and the second opening 107 includes a diameter D2, as shown in FIGS. 3 and 4. The diameter Dp is greater than the diameters D1 and D2 such as to leave an annular space 130 between inflatable plunger 116 and outer diameter of the central region 104, as shown in FIG. 6. The diameter Dp may be adjusted once the inflatable plunger 116 is inflated with an inflation medium, as further described below. The diameters D1 and D2 may be the same size or may be different sizes. In one embodiment, the diameter D1 is greater than D2; in other embodiments the diameter D2 is greater than D1. The sizes of the diameters D1 and D2 may be selected according to the implantation site 118 and the amount of blood flow through the first and second openings 105, 107, whereby small diameters may be selected for an increased size in the annular space 130 for increased blood flow. In the deflated and collapsed configuration, the inflatable plunger 116 includes a diameter Dd (see FIG. 12). In one embodiment, the diameter Dd includes a smaller diameter than diameters D1 and D2 for the first and second openings 105 and 107 when in the expanded configuration of the valve 100, such that the inflatable plunger 116 in the deflated configuration Dd may fit through the first or second openings 105, 107 when the valve 100 is in the expanded configuration De, as further explained below.

In the expanded configuration De, the inflatable plunger 116 is contained captive within the cage 102, as shown in FIG. 5. The inflatable plunger 116 is too large in the expanded configuration to pass through either of the first and second openings 105, 107 of the cage 102. The inflatable plunger 116 is also too large in the inflated configuration to pass through any of the expanded cells 112 even when the cage 102 is in its expanded configuration and maximal flow conditions through the longitudinal axis of the valve. In this embodiment of the valve 100, the inflatable plunger 116 is introduced into the cage 102 for inflation subsequent to expansion of the cage 102, as shown in FIG. 10. The inflatable plunger 116 may be inflated with an inflation medium including, for example, a gas, a liquid, or a hardening polymeric material. Subsequent to expansion, the inflatable plunger 116 remains inflated, as will be discussed more fully hereinbelow.

The cage 102 and the inflatable plunger 116 may be made from suitable materials including by way of example and not limitation, metal, pseudometal, and polymer material. In one embodiment, the cage 102 is monolithic and both the cage 102 and the inflatable plunger 116 are fabricated by vacuum deposition techniques. In accordance with the embodiments disclosed herein, the preferred deposition methodologies include ion-beam assisted evaporative deposition and sputtering techniques. In ion beam-assisted evaporative deposition, dual and simultaneous thermal electron beam evaporation may be employed with simultaneous ion bombardment of the substrate using an inert gas, such as argon, xenon, nitrogen or neon. Bombardment with an inert gas, such as argon ions serves to reduce void content by increasing the atomic packing density in the deposited material during deposition. The reduced void content in the deposited material is one of the important factors that allow the mechanical properties of that deposited material to be similar to the bulk material properties. Deposition rates up to 20 nanometers per second are achievable using ion beam-assisted evaporative deposition techniques.

The cage 102 and the inflatable plunger 116 may both be fabricated of a biocompatible metal and may be formed as a film of material. The cage 102 and the inflatable plunger 116 are not restricted to single layer films, but a plurality of films may be laminated to one another in order to enhance the material, geometric and/or functional properties of the resultant component. Suitable materials to fabricate the cage 102 and the inflatable plunger 116 are chosen for their biocompatibility, mechanical properties, i.e., tensile strength, yield strength, and their ease of deposition, include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

In one embodiment, the cage 102 is fabricated of metallic and/or pseudometallic films controlled to attain a regular, homogeneous atomic and molecular pattern of distribution along a portion of the central region 104 of the cage 102, which in this geometry is the luminal surface of the central region 104. This avoids the marked variations in surface composition, creating predictable oxidation and organic adsorption patterns and has predictable interactions with water, electrolytes, proteins and cells. Particularly, EC migration is supported by a homogeneous distribution of binding domains that serve as natural or implanted cell attachment sites, in order to promote unimpeded migration and attachment. Based on observed EC attachment mechanisms such binding domains should have a repeating pattern along the blood contact surface of no less than 1 micrometer radius and 2 micrometers border-to-border spacing between binding domains. Ideally, the inter-binding domain spacing is less than the nominal diameter of an endothelial cell in order to ensure that at any given time, a portion of an endothelial cell is in proximity to a binding domain.

In one embodiment, the inflatable plunger 116 is not expected to be endothelialized; rather, the inflatable plunger is non-thrombogenic. Metal construction of the inflatable plunger 116 will enhance geometrical regularity as metals have minimal molecular creep under increased strain. The maintenance of geometric regularity is important as the hydraulic closure depends on the regularity of the contact surface between the inflatable plunger 116 and a valve seat at the second end 108 of the cage 102. The use of composite constructions, including by way of example and not limitation, combinations of metal, polymers and or ceramic materials, may provide an increased burst pressure limit and lower surface thrombogenicity for the inflatable plunger 116.

Additionally, because the cage 102 and the inflatable plunger 116 may be fabricated of metal, one or both may be made more or less radiopaque by fabrication from a radiopaque metal, such as tantalum, or providing regions on the cage 102 and/or the inflatable plunger 116 that have a radiopaque metal differentially incorporated thereupon. Moreover, the cage 102 and the inflatable plunger 116 may be used either as a conductor of directly applied electrical energy or inductively energized by external application of energy, such as by ultrasound or magnetic resonance. This conductive property of the cage 102 and the inflatable plunger 116 may be particularly useful in diathermy, to return a signal for imaging without an added contrast medium, or return a signal to provide data concerning the in vivo environment. Conceivably, the kinetic energy of the inflatable plunger 116 can be converted into electrical energy to broadcast signals of quantitative hemodynamic parameters such as pressure and flow.

Figure 9:
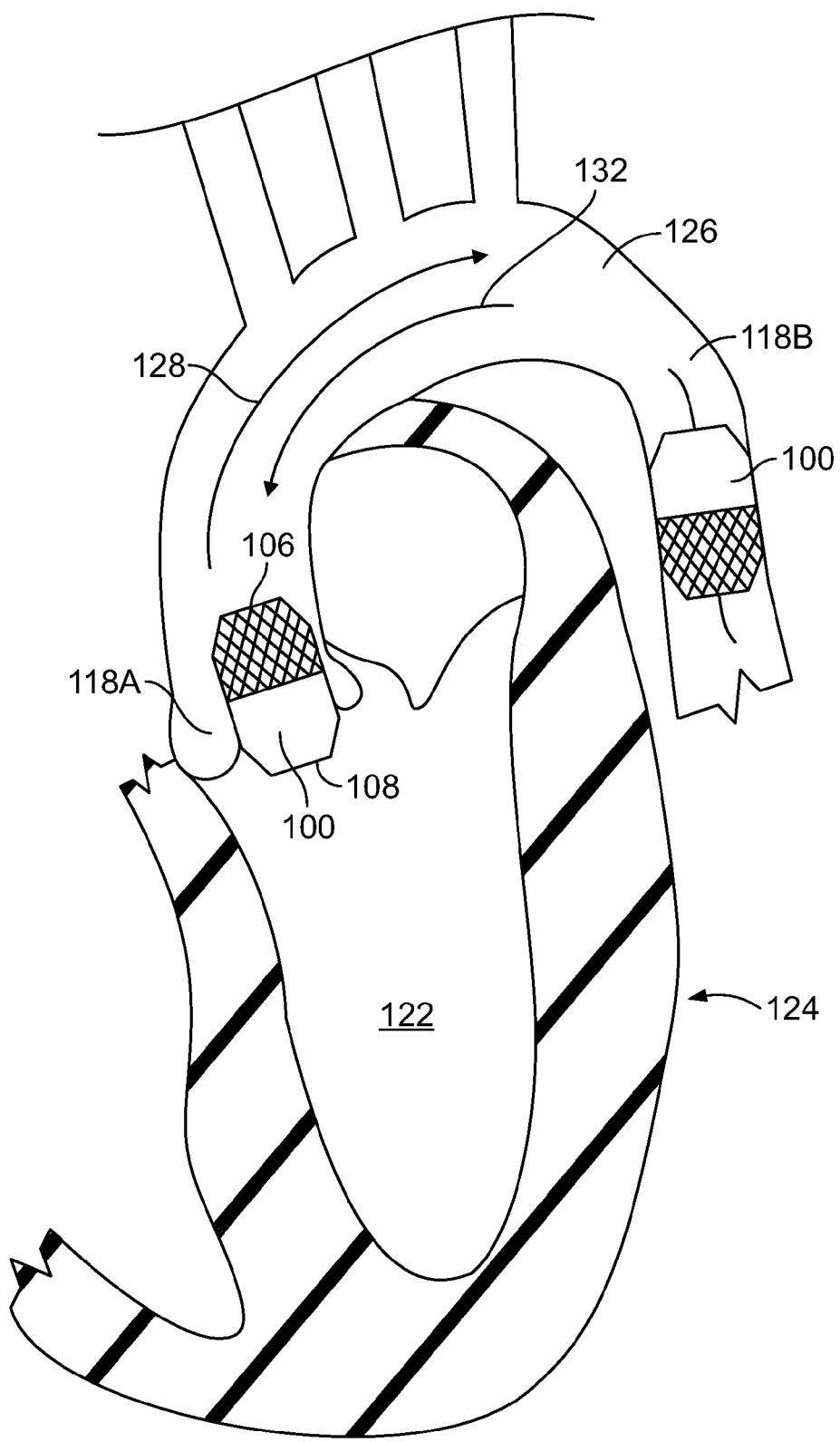
FIG. 9 is a schematic view of a cross-section of a heart illustrating implantation sites for the valve of FIG. 1.

Referring to FIGS. 5-9, operation of the valve 100 in the operational state will be described. The valve 100 is implanted at an implantation site 118, for example, at an anatomical site of a damaged cardiac valve 118a, or within the descending thoracic aorta 118b, as illustrated in FIG. 9. Upon implantation, the transluminal nature of the cage 102 in the expanded configuration fixes the cage in place within the cardiac valve 118a or the descending aorta 118b. Preferably, the central region 104 of the valve 100 is fixed into the respective implantation site 118. The cage 102 may include barbs 120 that expand radially outwardly upon expansion of the cage 102 into the expanded configuration. The barbs 120 penetrate luminal walls of the implantation site and provide resistance to motion of the cage 102 relative to the implantation site. Alternatively, the side walls of the central region 104 may be configured with a coating or alternative attachment mechanism to the implantation site, such as sutures, frictional coatings, and the like. Preferably, only the side walls of the central region 104 attach to the implantation site 118 as to allow normal blood flow through the implantation site 118.

Referring to FIG. 9, regardless of the site of implantation, orientation of the valve 100 is such that the second end 108 faces the left ventricle 122 of a heart 124. Upon contraction of the left ventricle 122, blood is forced out of the left ventricle 122 and into the aorta 126, as indicated by the arrow 128. Referring to FIG. 5, during this contraction, the blood flow pushes the inflatable plunger 116 toward the first end 106 of the cage 102. FIG. 6 illustrates the inflatable plunger 116 pushed to the first end 106 looking from the first end 106. An annular space 130 remains around the inflatable plunger 116. The constriction at the first end 106 constrains the inflatable plunger 116 from escaping the cage 102; however, blood flow through the first end 106 proceeds through expanded cells 112 of the annular space 130 at the first end 106. The expanded cells 112 can be maximized in area by eliminating struts 110 so as simplify the pattern. For example, around the first opening 105 at the first end 106, the expanded cells 112 can transition into radially oriented struts 110, such that a minimum of 3 struts 110 will join the first opening 105.

Upon relaxation of the left ventricle, or ventricular diastole, the direction of blood flow reverses from the aorta into the left ventricle, as indicated by the arrow 132 in FIG. 9. Referring to FIG. 7, during diastole the blood flow pushes the inflatable plunger 116 toward the second end 108 of the cage 102. The blood impervious region 114 is disposed at the second end 108, so the constriction at the second end 108 constrains the inflatable plunger 116 from escaping the cage 102 and thereby impedes blood flow through the second end 108. It is contemplated that the effectiveness with which the second end 108 prevents regurgitant blood flow is related to the quality of seal achieved between the inflatable plunger 116 and the luminal surface of the second opening 107 at the second end 108.

Referring to FIG. 10, delivery and deployment of the valve 100 to the implantation site 118 may utilize a guidewire 134 operably coupled with an inflation catheter 146 coaxially placed within the lumen 103 of the valve 100 and through the first opening 105 and the second opening 107. The guidewire 134 is percutaneously advanced through an accessing vessel 136 such that the guidewire 134 extends distally beyond implantation site 118. Implantation to the damaged ventricular valve site 118a may be achieved through a trans-arterial or transcardiac approach, which are retrograde or antegrade respectively. In the retrograde approach, the orientation of the cage 102 would be as illustrated in FIG. 10 such that the second end 108 is nearer a distal end 138 of a catheter sheath 140 concentrically coupled over the valve 100 in the collapsed configuration. In the antegrade approach (trans-apical or trans-septal), the orientation of the cage 102 illustrated in FIG. 10 would be reversed such that the first end 106 is nearer the distal end 138 of the catheter sheath 140 than is the second end 108. Implantation to the descending aorta site 118b may be achieved through upper or lower extremity arterial access, in which case the cage 102 would be oriented relative to the catheter sheath 140 as illustrated in FIG. 10.

In one method for implantation of the valve 100 in the delivery state, the cage 102 and the blood impervious region 114 has a collapsed or contracted configuration with diameter Dc concentrically contained within a lumen 142 of the catheter sheath 140, as illustrated in FIG. 10. For minimizing the stress on a patient during delivery, the catheter sheath 140 preferably has an outer diameter of about 12-14 French or less. The cage 102 may be self-expanding or balloon expandable via an inflation balloon 144 coaxially coupled to the interior surface of the cage 102 and the blood impervious region 114. In one embodiment, the cage 102 is crimped onto the inflation balloon 144 in a way similar to the crimping of a regular balloon-expandable stent. The inflation balloon 144 is attached to and in fluid communication with an inflation catheter 146 that is disposed longitudinally through the catheter sheath 140.

With the cage 102 loaded into the catheter sheath 140, the catheter sheath 140 may be advanced percutaneously into a patient until the cage 102 is disposed at the implantation site 118. The inflation balloon 144 may be attached to a distal end 148 of the inflation catheter 146. In one embodiment, the inflation catheter 146 includes a guidewire lumen 152 disposed longitudinally along a length of the inflation catheter 146 for guiding the inflation catheter 146 over the guidewire 134. In another embodiment, the inflation catheter 146 includes an over-a-wire rapid access port 150 and the guidewire lumen 152 for guiding the inflation catheter 146 over the guidewire 134, as illustrated in FIG. 10. An inflation lumen 154 is disposed longitudinally through the inflation catheter 146 for delivery of an inflation medium to the inflation balloon 144. An example of the over-a-wire rapid access inflation catheter 146 described in FIG. 10 may be found, for example, in U.S. Pat. No. 5,626,600. Another example of an over-a-wire inflation catheter having a similar geometry is disclosed, for example, in U.S. Pat. No. 5,232,445.

Radiopaque markers, fluoroscopy, transesophageal echocardiography, or other methods known in the art may be used to determine the exact position of the cage 102 relative to the implantation site 118. At this point in the method, the heart may be rapid paced or made to beat at a rapid pace to minimize motion at the implantation site. Minimizing motion at the implantation site is helpful to the medical professional in the accurate and secure placement of the cardiac valve 100 at the implantation site 118. The rapid pacing can be achieved by electronic or chemical stimulus of the heart muscles.

Next, the catheter sheath 140 is translated proximally relative to the inflation catheter 146, as indicated by arrow 156 in FIG. 10, until the cage 102 is free from being contained within the lumen 142. Upon exiting the catheter sheath 140, the cage 102 may be deployed to the expanded configuration to diameter De by inflating the balloon 144 with an inflation medium. If the cage 102 is self-expanding, it will still require post deployment dilatation with the inflation balloon 144 to achieve adequate setting of the cage 102 at the site of implantation 118. Once the cage 102 has been deployed into the expanded configuration at the implantation site 118, the inflation catheter 146 and the inflation balloon 144 are proximally withdrawn from the valve 100.

In one embodiment, the inflation catheter 146 is withdrawn from the access vessel 136 without withdrawal of the guidewire 134, as illustrated in FIG. 11. This is because the guidewire 134 remains correctly situated in passing through the first and second openings 105, 107 of the cage 102. However, if the guidewire 134 is withdrawn with the inflation catheter 146, reinsertion of the guidewire 134 may be problematic in that the guidewire 134 may incorrectly and undesirably pass through an expanded cell 112 proximate the first end 106 of the cage 102 instead of passing through the first opening 105.

Figure 12:
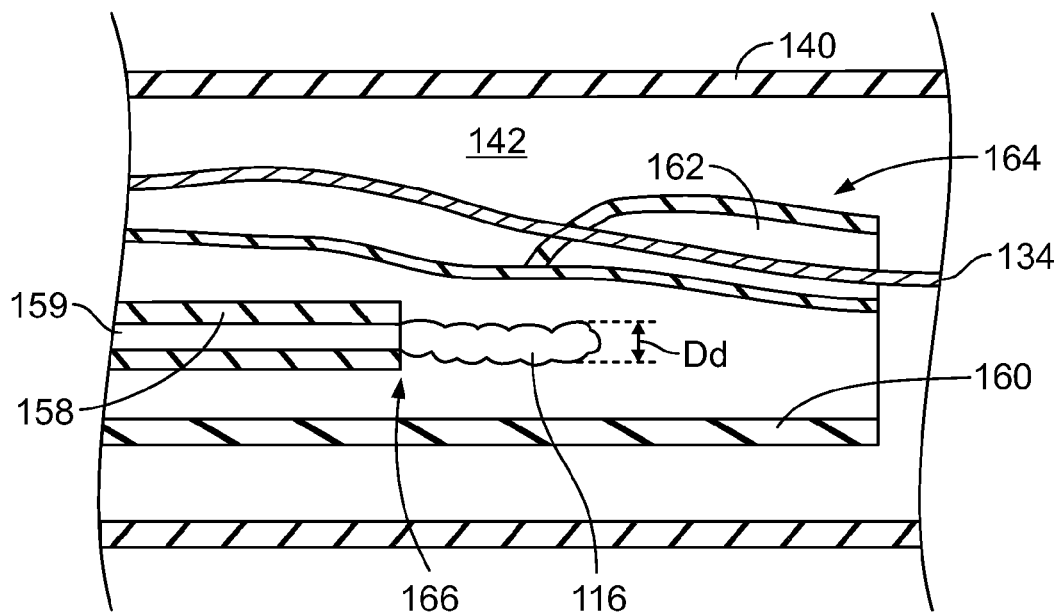
FIG. 12 is a cross-sectional view of an inflation catheter disposed within an over-a-wire second catheter sheath disposed within an outer catheter sheath.
Figure 13:
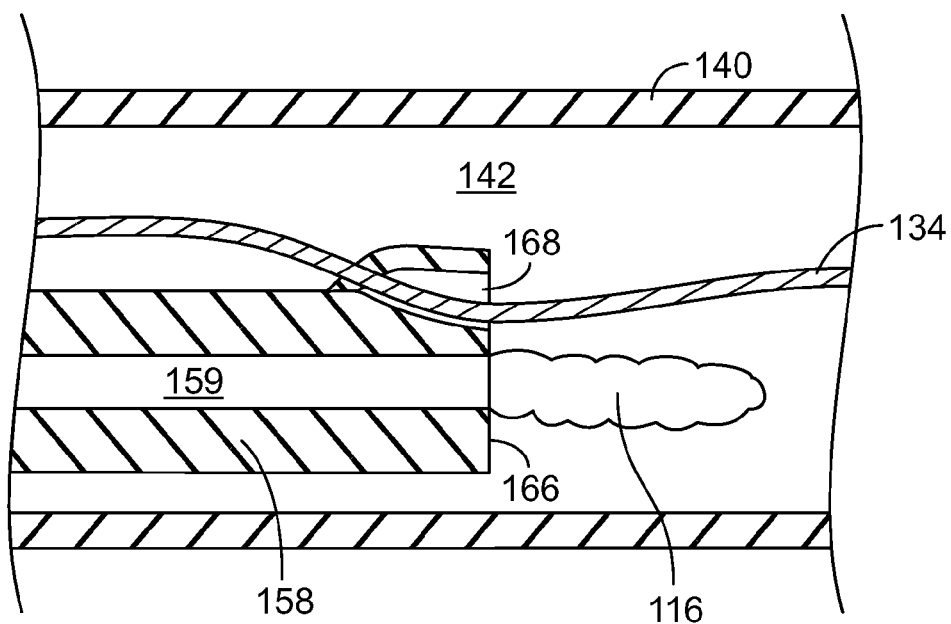
FIG. 13 is a cross-sectional view of an over-a-wire inflation catheter disposed within the outer catheter sheath of FIG. 12.

As illustrated in FIG. 12, a second inflation catheter 158 carrying the inflatable plunger 116 in a deflated and collapsed configuration Dd is introduced into the catheter sheath 140. In one embodiment, the second inflation catheter 158 may be introduced into the catheter sheath 140, for example, within a second catheter sheath 160 coaxially placed within the catheter sheath 140. In one embodiment, the second catheter sheath 160 is an over-a-wire rapid access catheter sheath and includes a lumen 162 disposed longitudinally through a wall at a distal end 164 thereof. The lumen 162 accommodates the guidewire 134, which extends external to the second catheter sheath 160 except at the distal end 164. This arrangement is a widely used method known in the art for advantageously allowing for use of a shorter guidewire 134 and for a single operator to exchange such catheters at arms length. In another embodiment, the second inflation catheter 158 may, for example, be introduced directly into the catheter sheath 140, as illustrated in FIG. 13. In this embodiment, the second inflation catheter 158 is an over-a-wire inflation catheter including a rapid-exchange type distal end 166 including a guidewire lumen 168.

Figure 14:
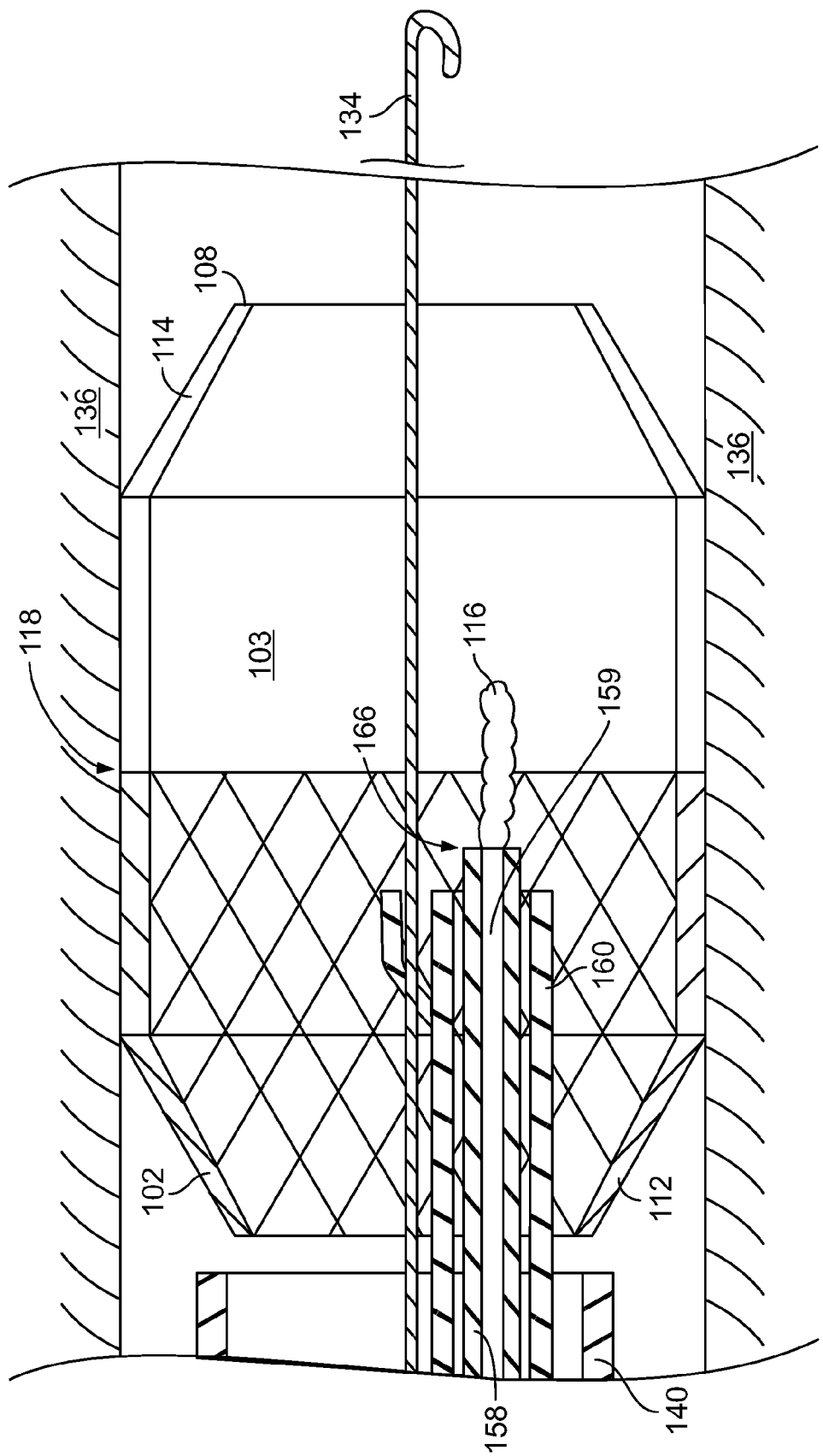
FIG. 14 is a cross-sectional view of a plunger being disposed within a cage in an expanded configuration.

The inflatable plunger 116 is disposed on the distal end 166 of the second inflation catheter 158 and is in fluid communication with a lumen 159 within the second inflation catheter 158, as illustrated in FIGS. 12 and 13. The second inflation catheter 158 is advanced through the lumen 142 of the catheter sheath 140, either within the second catheter sheath 160, as illustrated in FIG. 14, or directly utilizing the configuration illustrated in FIG. 13, such that the inflatable plunger 116 is disposed in the lumen 103 within the cage 102 and the blood impervious region 114. Again, radiopaque markers, fluoroscopy, transesophageal echocardiography, or other methods known in the art may be used to determine the exact position of the inflatable plunger 116 relative to the cage 102.

When the inflatable plunger 116 is positioned as desired within the lumen 103 of the cage 102 and the blood impervious region 114, the inflatable plunger 116 is inflated to the expanded configuration with diameter Dp with an inflation medium disposed through the lumen 159 of the second inflation catheter 158. The expanded configuration of the inflatable plunger 116 may be, for example, a generally ball-shaped configuration. The inflation medium used to inflate the inflatable plunger 116 should have a density similar to that of blood and a low mass (weight). The mass affects the acceleration and deceleration of the inflatable plunger 116 in an inverse relationship in accordance to the second law of Newton; therefore, the lower the mass the higher the frequency of reciprocal movement the inflatable plunger 116 can achieve. In one embodiment, the inflatable plunger 116 is inflated with inflation medium including a density between about 1025 and 1125 kg/m$^3$.

Following inflation, the inflatable plunger 116 is detached from the distal end 166 of the second inflation catheter 158 using a detachment device, including by way of example and not limitation, a threaded fitting, a quick-connect fitting, or other inflation fitting in combination with a one-way valve. The inflatable plunger 116 remains inflated upon detachment of the second inflation catheter 158 via a valve in the surface of the inflatable plunger 116. Upon removal of the guidewire 134, the second inflation catheter 158 and the catheter sheath 140 (and the second catheter sheath 160, if used) from the patient, the cardiac valve 100 has been deployed in the operational state and may begin operation as described hereinabove with regard to FIGS. 5-9.

Figure 15:
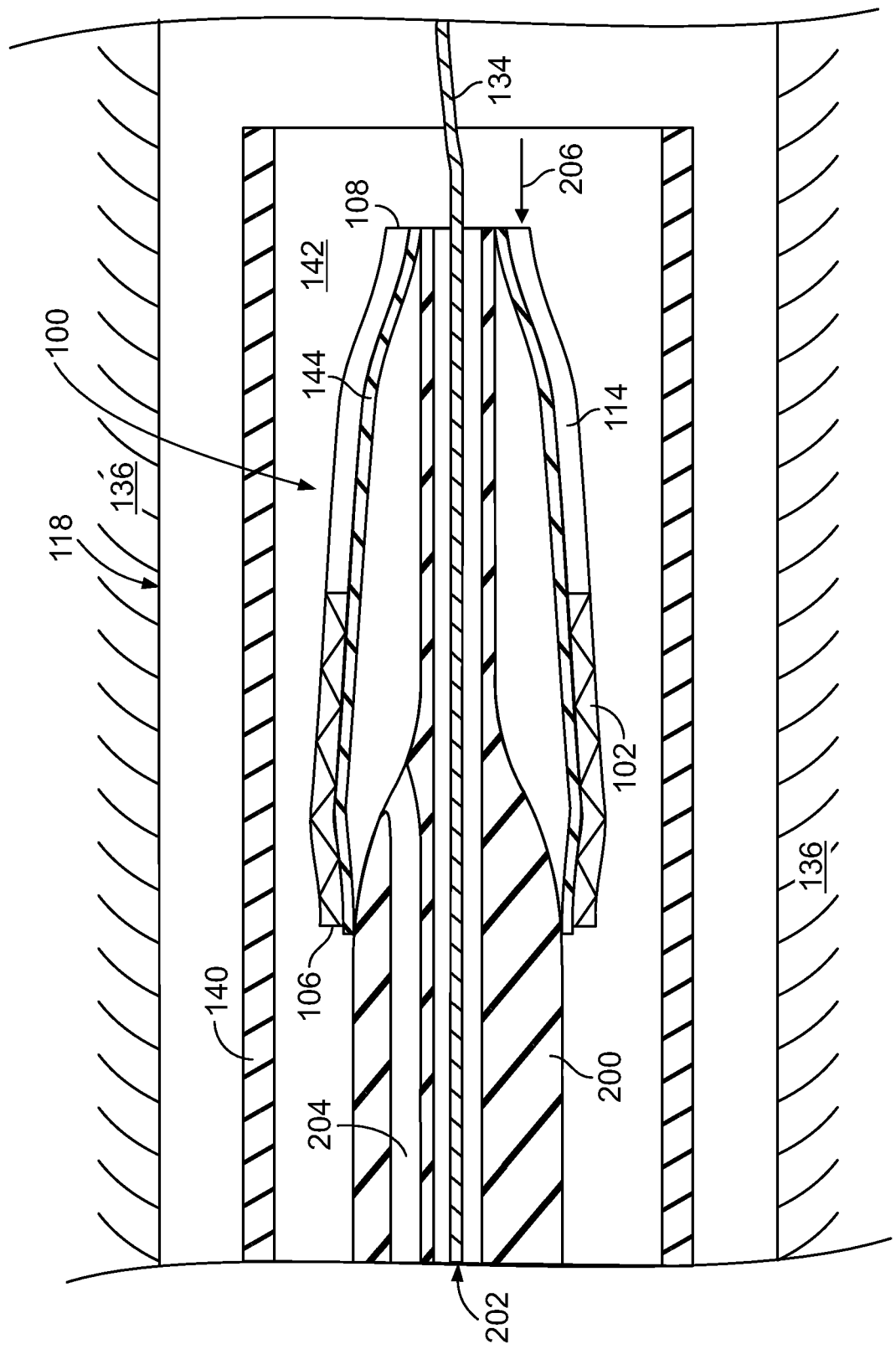
FIG. 15 is a cross-sectional view of a step in an embodiment of a method for delivery of the valve of FIG. 1.
Figure 16:
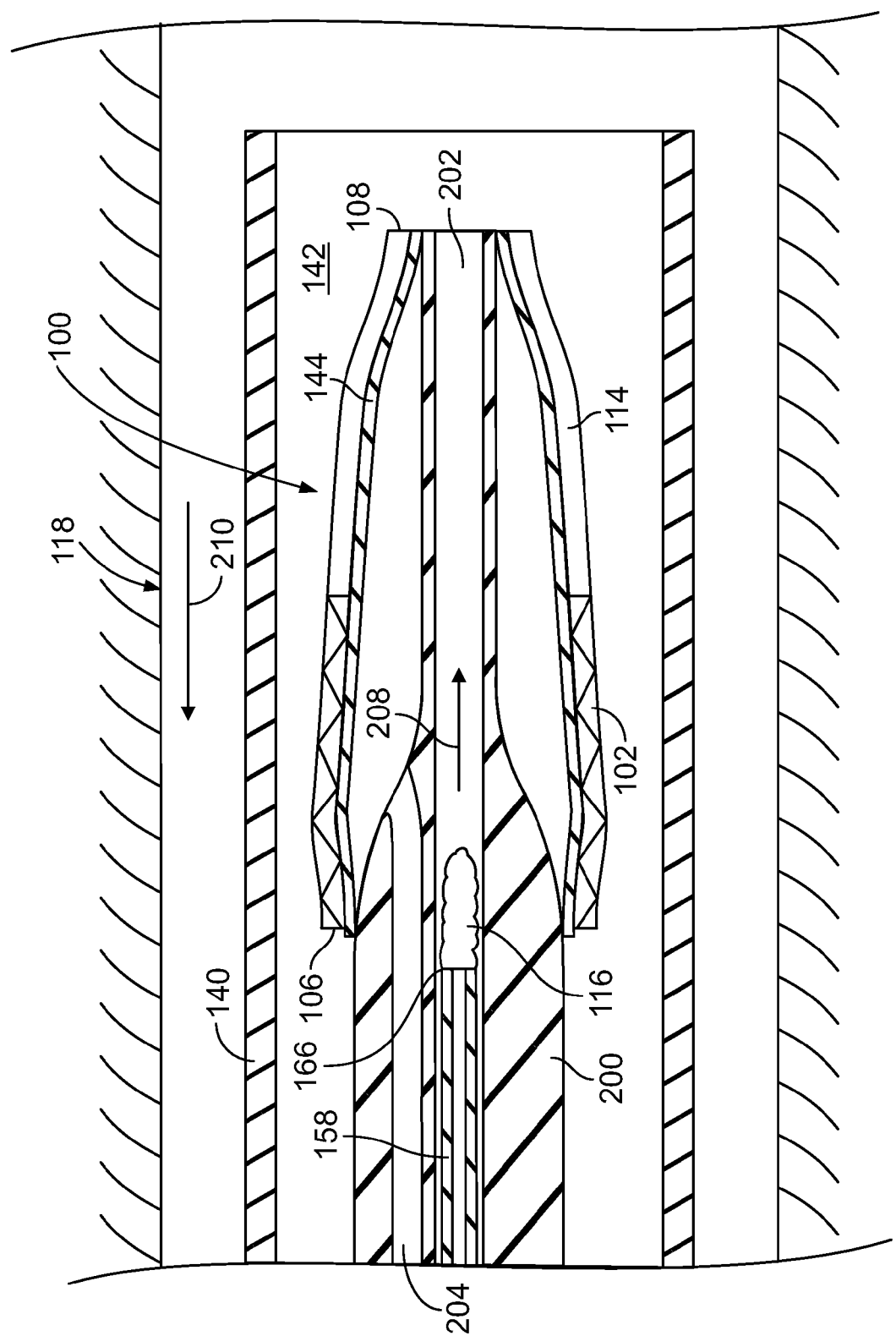
FIG. 16 is a cross-sectional view of another step in the method of FIG. 15 for delivery of the valve of FIG. 1.
Figure 17:
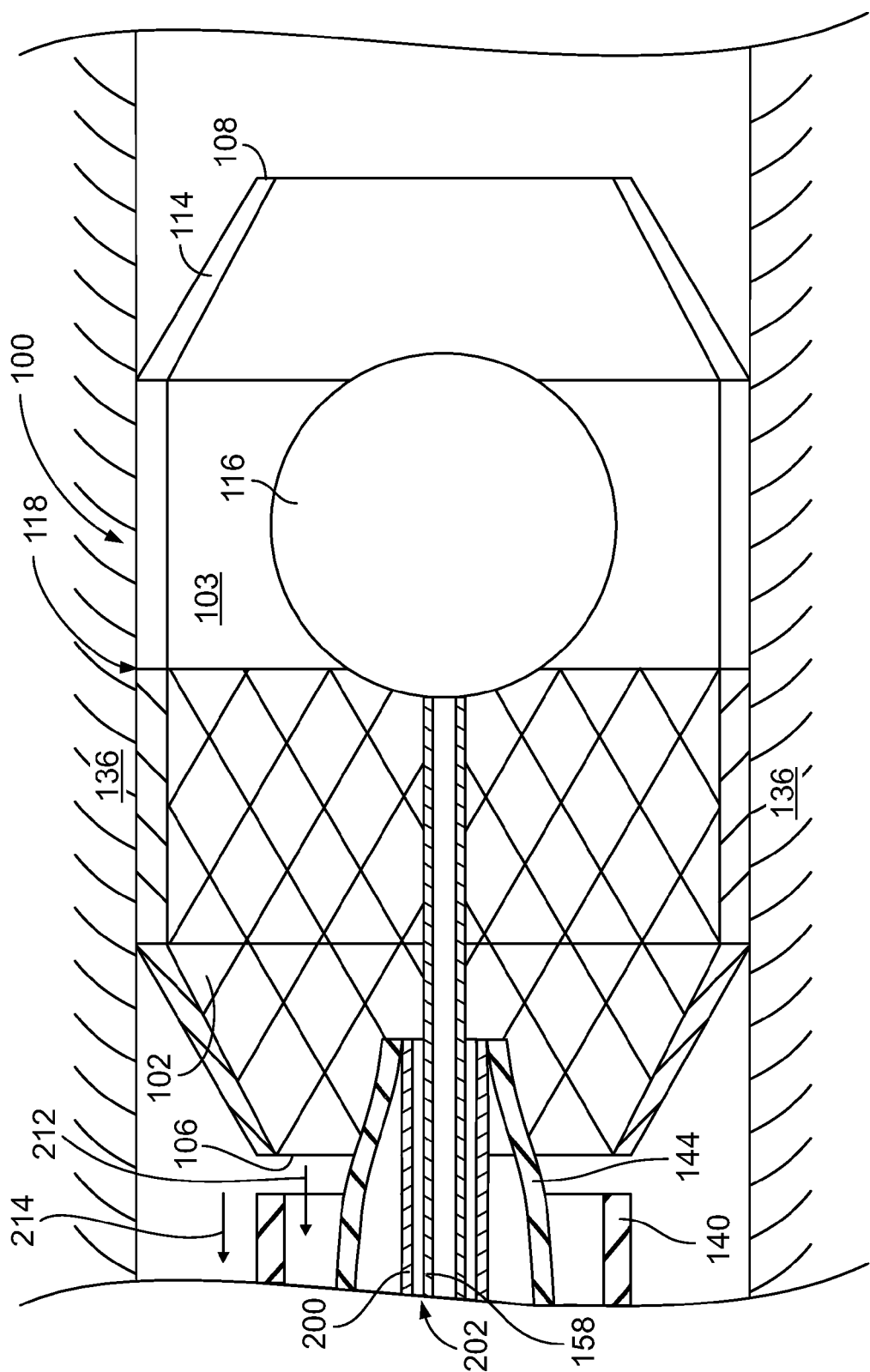
FIG. 17 is a cross-sectional view of a further step in the method of FIG. 15 for delivery of the valve of FIG. 1.

Referring to FIGS. 15-17, another embodiment of a method for delivery and deployment of the valve 100 to the implantation site 118 utilizes a third inflation catheter 200 for delivery of the cage 102. The third inflation catheter 200 includes a centrally disposed guidewire lumen 202 that is large enough to accommodate the second inflation catheter 158. In this method, the cage 102 is crimped onto the inflation balloon 144, which is attached to the third inflation catheter 200 and in fluid communication therewith via a third inflation lumen 204 disposed longitudinally through the third inflation catheter 200. In preparation for delivery and deployment of the cage 102, the third inflation catheter 200, including the cage 102 and inflation balloon 144 attached thereto, is disposed longitudinally through the catheter sheath 140.

Referring to FIG. 15, following percutaneous insertion of the guidewire 134 to beyond the implantation site 118, the catheter sheath 140 and the third inflation lumen 200 within are advanced percutaneously over the guidewire 134 until the cage 102 is disposed at the implantation site 118. Radiopaque markers, fluoroscopy, transesophageal echocardiography, or other methods known in the art may be used to determine the exact position of the cage 102 relative to the implantation site 118. At this point in the method, the heart may be rapid paced or made to beat at a rapid pace to minimize motion at the implantation site 118. Further, after final positioning of the cage 102, but before the inflation balloon 144 is inflated, the guidewire 134 may pulled proximally out of the accessing vessel 136, as illustrated by arrow 206 in FIG. 15, thus leaving the guidewire lumen 202 empty.

Referring to FIG. 16, in the next step in this embodiment of the method, the second inflation catheter 158 is coaxially advanced through the guidewire lumen 202 to the implantation site 118, as indicated by arrow 208 in FIG. 16. Again, radiopaque markers, fluoroscopy, transesophageal echocardiography, or other methods known in the art may be used to determine the exact position of the inflatable plunger 116 relative to the cage 102 and/or the implantation site 118. Next, the catheter sheath 140 is translated proximally relative to the third inflation catheter 200, as indicated by arrow 210 in FIG. 16, until the cage 102 and the blood impervious region 114 are free from being contained within the lumen 142. Upon exiting the catheter sheath 140, the cage 102 may be deployed to the expanded configuration by inflating the inflation balloon 144 with an inflation material disposed through the second inflation catheter 158, as previously described.

Referring to FIG. 17, following deployment of the cage 102, the inflation balloon 144 is deflated and withdrawn from the cage 102 as indicated by arrow 212, leaving the inflatable plunger 116 in the deflated configuration within the cage 102. The inflatable plunger 116 is inflated to the expanded configuration with diameter Dp with fluid via the second inflation catheter 158 within the lumen 103 of the valve 100. Following inflation, the inflatable plunger 116 is detached from the second inflation catheter 158 and remains inflated upon detachment of the second inflation catheter 158, as described hereinabove with regard to the method of FIG. 14. Upon removal of the second inflation catheter 158, the third inflation catheter 200, and the catheter sheath 140 from the accessing vessel 136, as indicated by arrow 214 in FIG. 17, the cardiac valve 100 has been deployed in the operational state and may begin operation as described hereinabove with regard to FIGS. 5-9.

Figure 18:
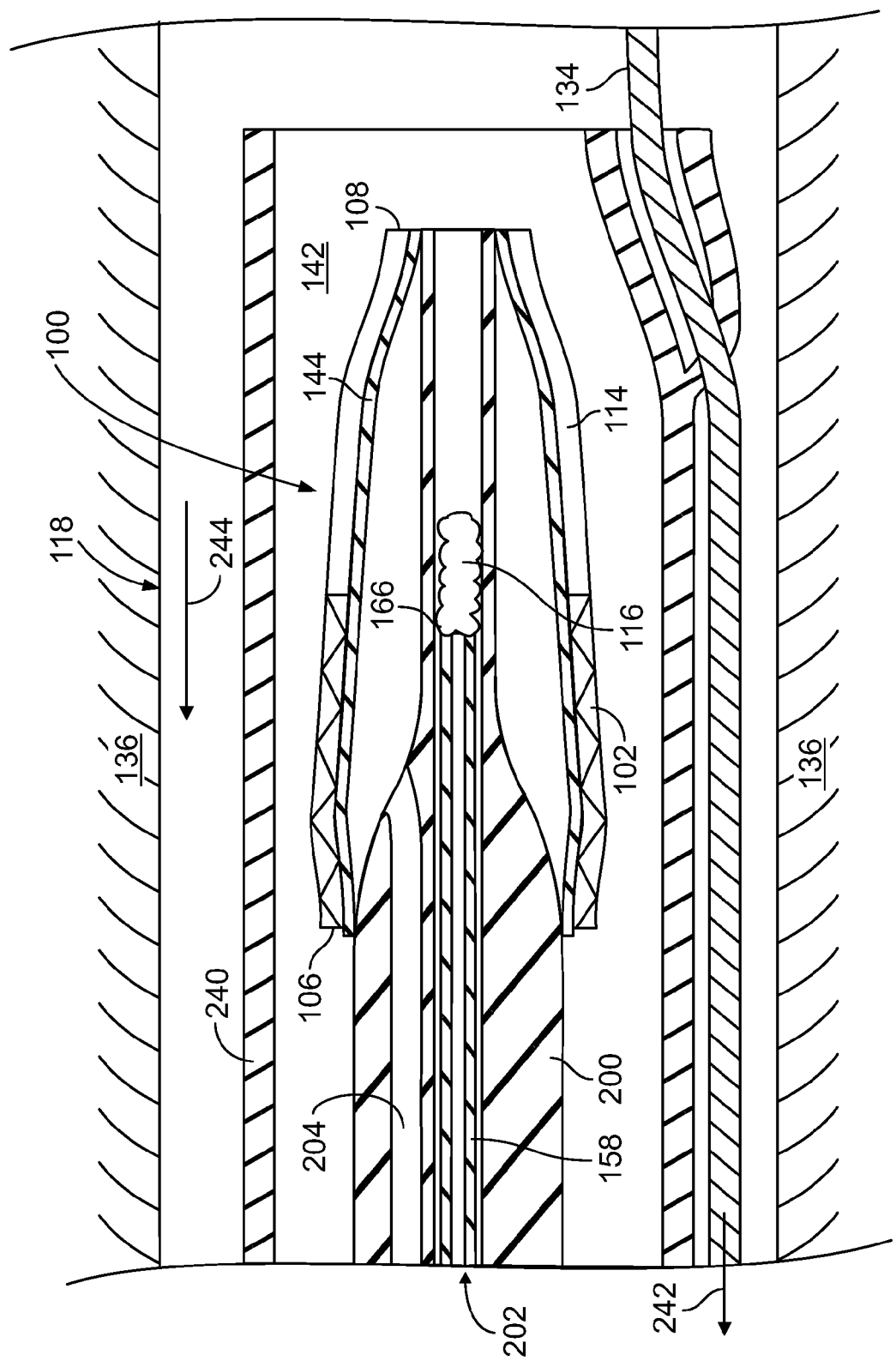
FIG. 18 is a cross-sectional view of a step in another embodiment of a method for delivery of the valve of FIG. 1.
Figure 19:
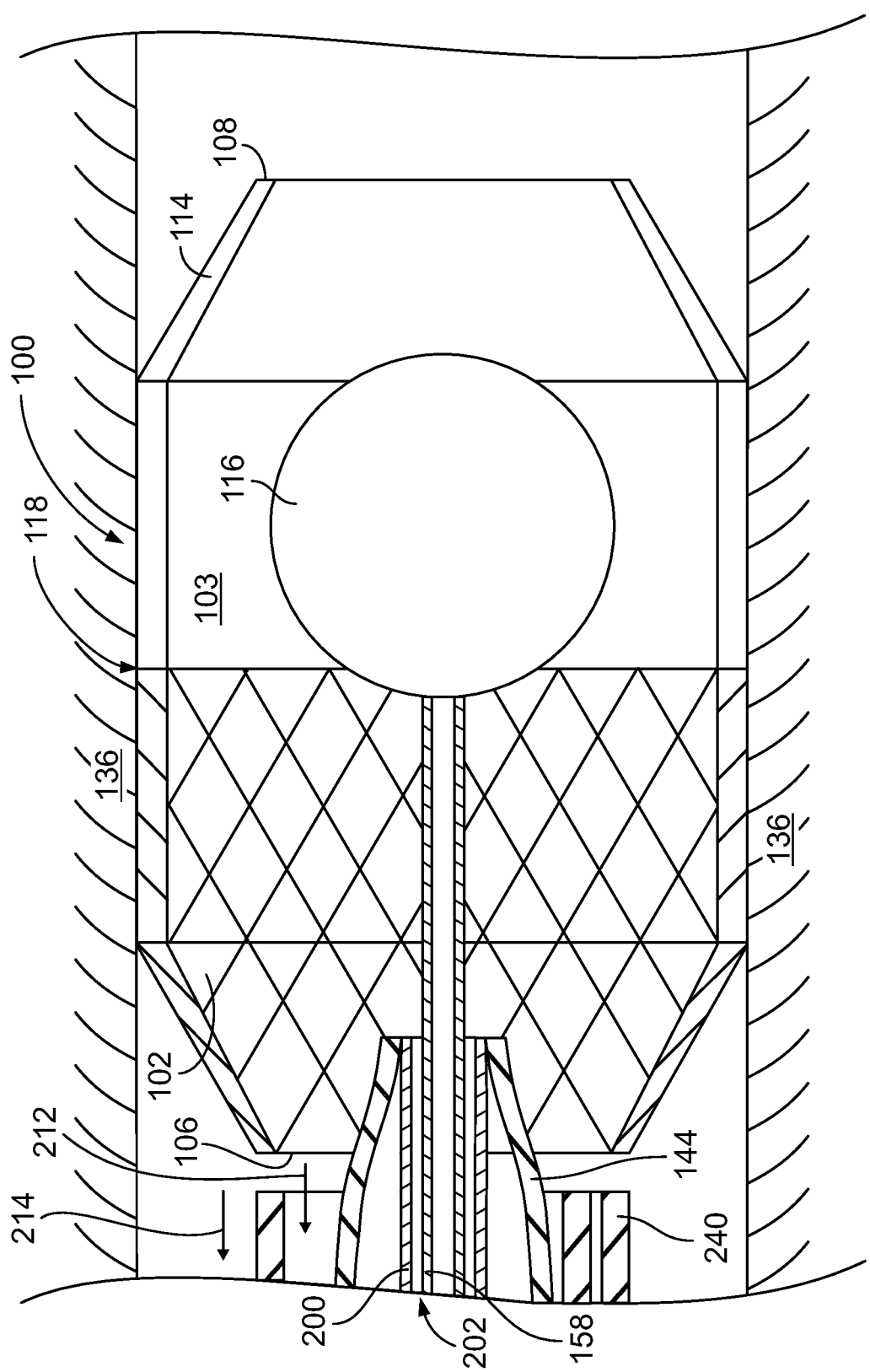
FIG. 19 is a cross-sectional view of another step in the method of FIG. 18 for delivery of the valve of FIG. 1.

Referring to FIGS. 18 and 19, a further method for delivery and deployment of the valve 100 to the implantation site 118 is similar to the method described with regard to FIGS. 15-17 except for the following differences. In this method, an over-a-wire rapid access catheter sheath 240 replaces the catheter sheath 140. In preparation for delivery and deployment, the third inflation catheter 200, including the cage 102 and inflation balloon 144 attached thereto, is disposed longitudinally through the catheter sheath 240.

Referring to FIG. 18, following percutaneous insertion of the guidewire 134 to beyond the implantation site 118, the over-a-wire rapid access catheter sheath 240 is advanced percutaneously over the guidewire 134 until the cage 102 is disposed at the implantation site 118. After final positioning of the cage 102, but before the inflation balloon 144 is inflated, the guidewire 134 may be pulled proximally out of the accessing vessel 136, as illustrated by arrow 242 in FIG. 18. If the guidewire 134 is not removed at this point, subsequent expansion of the cage 102 would undesirably trap the guidewire 134 between the cage 102 and a luminal surface of the implantation site 118. Such entrapment of the guidewire 134 may cause undesirable movement of the cage 102 when the guidewire 134 is ultimately withdrawn.

In one embodiment, as illustrated in FIG. 18, the second inflation catheter 158 including the inflatable plunger 116 attached at the distal end 166 thereof is disposed longitudinally through the lumen 202 of the third inflation catheter 200 prior to insertion of the over-a-wire rapid access catheter sheath 240 into the accessing vessel 136. In another embodiment, the second inflation catheter 158 including the inflatable plunger 116 attached at the distal end 166 thereof is advanced through the lumen 202 of the third inflation catheter 200 subsequent to insertion of the over-a-wire rapid access catheter sheath 240 into the accessing vessel 136, as described hereinabove with regard to FIG. 16.

Still referring to FIG. 18, the catheter sheath 240 is translated proximally relative to the third inflation catheter 200, as indicated by arrow 244, until the cage 102 is free from being contained within the lumen 142. Upon exiting the catheter sheath 240, the cage 102 may be deployed to the expanded configuration by inflating the inflation balloon 144. Referring to FIG. 19, following deployment of the cage 102, the inflation balloon 144 is deflated and withdrawn from the cage 102 as indicated by arrow 212, leaving the inflatable plunger 116 in the deflated configuration within the cage 102. Following inflation of the inflatable plunger 116, the second inflation catheter 158, the third inflation catheter 200, and the catheter sheath 240 are withdrawn from the accessing vessel 136, as indicated by the arrow 214 in FIG. 19. At this point, the cardiac valve 100 has been deployed in the operational state and may begin operation as described hereinabove with regard to FIGS. 5-9.

Referring to FIGS. 20-23, another embodiment of a method for the delivery and deployment of the valve 100 to the implantation site 118 is similar to the embodiment described hereinabove with regard to FIGS. 15-17 except for the following differences. In this embodiment, the cage 102 and the inflatable plunger 116 are delivered to the implantation site 118 via first and second lumens 302, 304, respectively, of a double lumen sheath 300. A balloon inflation catheter 312 including the inflation balloon 144 and the cage 102 disposed thereon is disposed within the first lumen 302 and the second inflation catheter 158 including the inflatable plunger 116 disposed thereon is disposed within the second lumen 304.

Figure 20:
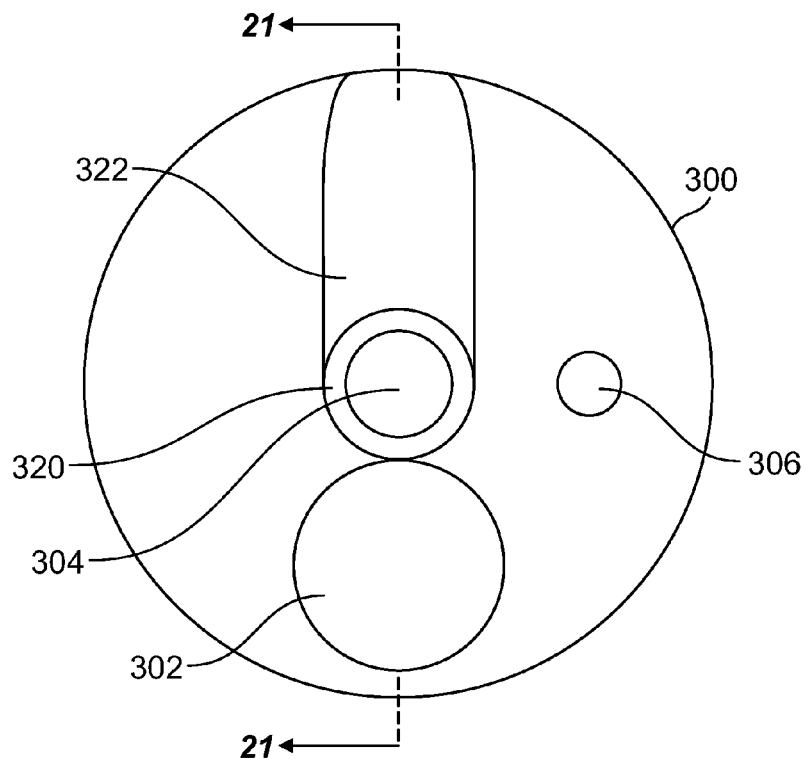
FIG. 20 is an end-on view of a distal end of a catheter sheath useful in a further embodiment of a method for delivery of the valve of FIG. 1.

Referring to FIG. 20, a guidewire lumen 306 is disposed longitudinally along a length of the double lumen sheath 300 for guiding the double lumen sheath 300 over the guidewire 134. The double lumen sheath 300 may be a conventional sheath including the guidewire lumen 306 extending entirely therethrough or the double lumen sheath 300 may be an over-a-wire rapid access sheath including the guidewire lumen 306 extending through only a portion of the double lumen sheath 300. The double lumen sheath 300 may be generally cylindrical including a longitudinally extending central axis, as illustrated by center line 308 in FIGS. 21-23.

Figure 21:
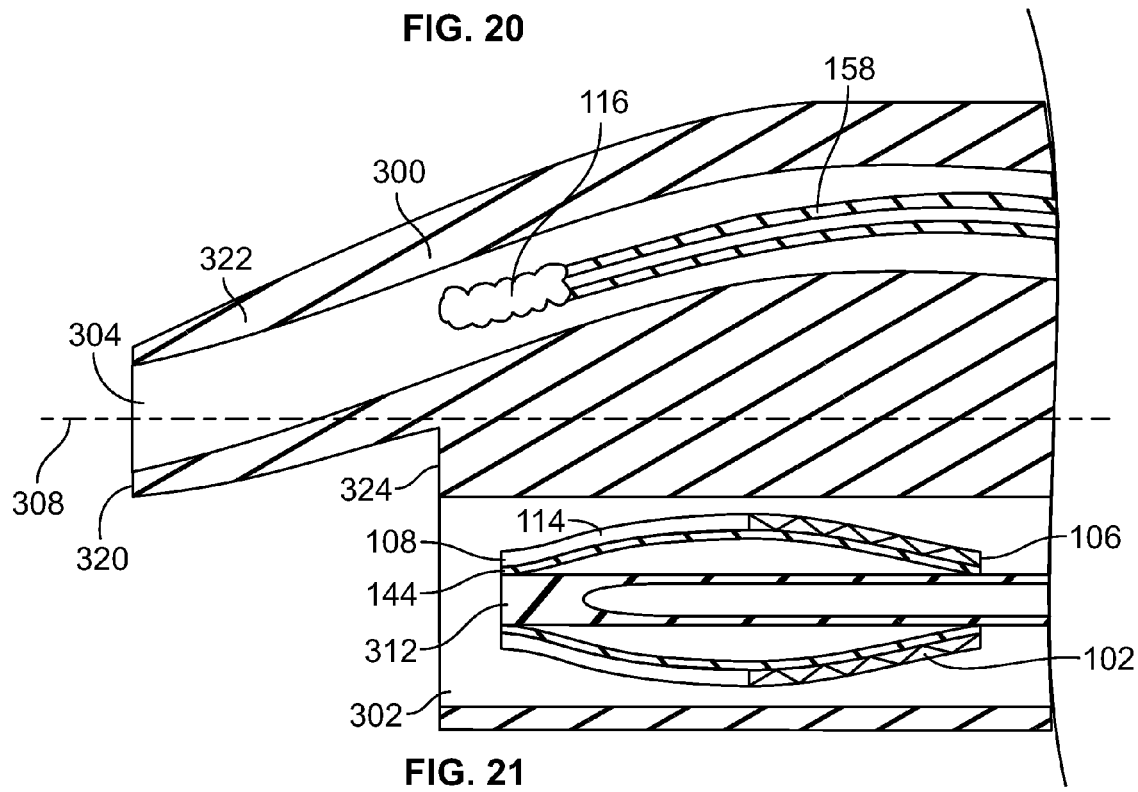
FIG. 21 is a cross-sectional view of the catheter sheath of FIG. 20 taken generally along the line 21-21 of FIG. 20.
Figure 22:
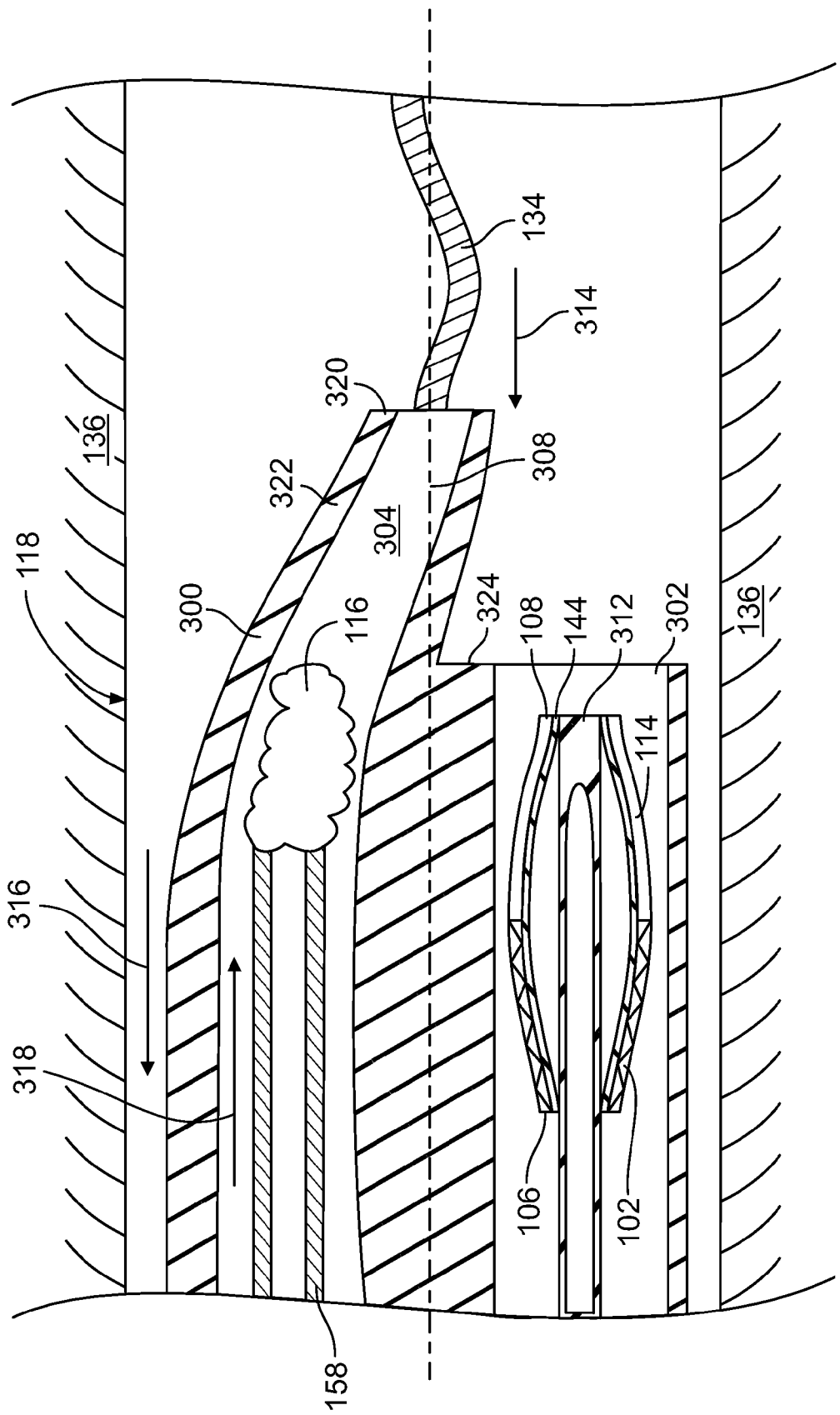
FIG. 22 is a cross-sectional view of a step in a further embodiment of a method for delivery of the valve of FIG. 1.

Referring to FIG. 22, following percutaneous insertion of the guidewire 134 to beyond the implantation site 118, the double lumen sheath 300 is advanced percutaneously over the guidewire 134 until the cage 102 is disposed at the implantation site 118. In this embodiment, because of the geometry of the guidewire lumen 306 relative to the first and second lumens 302, 304, the guidewire 134 is illustrated in FIG. 22 as emerging from behind the double lumen sheath 300. In other embodiments, the guidewire lumen 306 may be positioned through the double lumen sheath 300 in other orientations relative to the first and second lumens 302, 304, it being understood that the orientation illustrated in FIGS. 20-22 is exemplary only and not limiting.

In one embodiment of the method, as illustrated in FIGS. 21 and 22, both the balloon inflation catheter 312 and the second inflation catheter 158 are disposed within the double lumen sheath 300 prior to insertion of the double lumen sheath 300 into the accessing vessel 136. In other embodiments, one or both of the balloon inflation catheter 312 and the second inflation catheter 158 may be advanced through the double lumen sheath 300 subsequent to insertion of the double lumen sheath 300 into the accessing vessel 136. Radiopaque markers, fluoroscopy, transesophageal echocardiography, or other methods known in the art may be used to determine the exact position of the cage 102 and/or the inflatable plunger 116 relative to the implantation site 118 or to one another.

At this point in the method, the heart may be rapid paced or made to beat at a rapid pace to minimize motion at the implantation site 118. After final positioning of the cage 102, but before the inflation balloon 144 is inflated, the guidewire 134 may be pulled proximally out of the double lumen sheath 300, as indicated by arrow 314 in FIG. 22. If the guidewire 134 is not removed at this point, subsequent expansion of the cage 102 would undesirably trap the guidewire 134 between the cage 102 and a luminal surface of the implantation site 118. Following withdrawal of the guidewire 134, the double lumen sheath 300 is translated proximally relative to the balloon inflation catheter 312, as indicated by arrow 316 in FIG. 22, until the cage 102 is free from being contained within the lumen 302. Upon exiting the double lumen sheath 300, the cage 102 may be deployed to the expanded configuration by inflating the inflation balloon 144.

Figure 23:
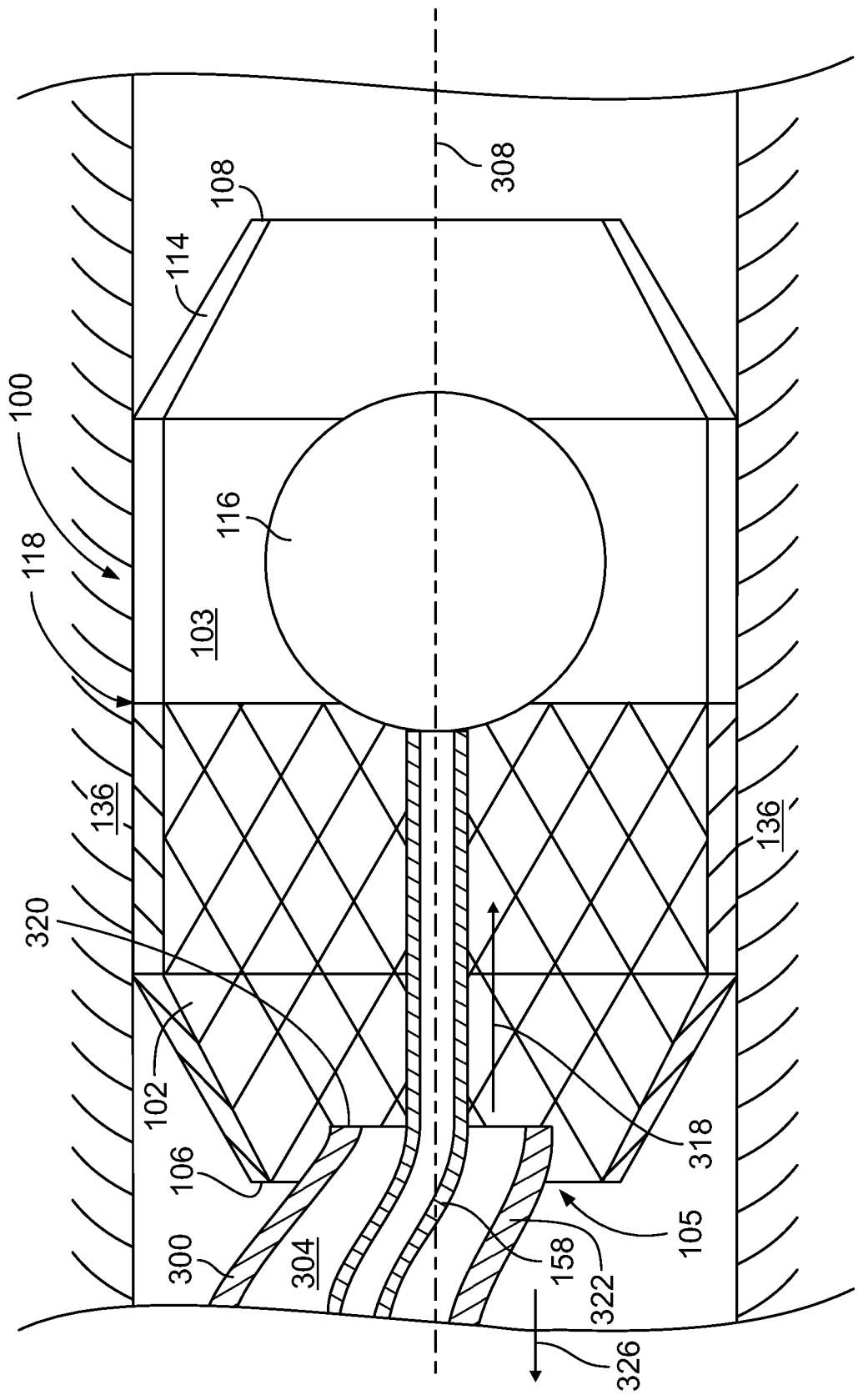
FIG. 23 is a cross-sectional view of another step in the method of FIG. 22 for delivery of the valve of FIG. 1.

Referring to FIG. 23, following deployment of the cage 102, the inflation balloon 144 is deflated and withdrawn from the cage 102 back into the first lumen 302. It is desirable for a distal end 320 of the second lumen 304 to be aligned with the first opening 105 disposed through the first end 106 of the cage 102 to facilitate introduction of the inflatable plunger 116 into the cage 102. To this end, in one embodiment, the double lumen sheath 300 includes a centering projection 322 extending beyond a distal end 324 end thereof. The double lumen sheath 300 may be advanced distally such that the centering projection 322 enters the cage 102 through the first opening 105. Next, the second inflation catheter 158 is translated distally relative to the double lumen sheath 300, as indicated by arrow 318 in FIGS. 22 and 23, thus delivering the inflatable plunger 116 in the deflated configuration within the cage 102. In embodiments not including the centering projection 322, the double lumen sheath 300 may be left a short distance from the first opening 105 to allow the second inflation catheter 158 to be guided into the cage 102 via radiopaque markers, fluoroscopy, transesophageal echocardiography, or other methods known in the art.

Following inflation of the inflatable plunger 116, the second inflation catheter 158 may be withdrawn back into the second lumen 304 and the double lumen sheath 300 may be withdrawn from the accessing vessel 136, as indicated by the arrow 326 in FIG. 23. At this point, the cardiac valve 100 has been deployed in the operational state and may begin operation as described hereinabove with regard to FIGS. 5-9.

As described herein, a method for deployment of a transluminal cardiac valve, the cardiac valve including an operational state comprising a generally tubular cage disposed in an expanded configuration having a generally uniform central region, first and second ends each diametrically constricted relative to the central region, and a blood impervious region extending from the first end of the cage to within the generally uniform central region, and an inflatable plunger freely disposed and captured within the cage when inflated, and a delivery state including the generally tubular cage disposed in a collapsed configuration and crimped onto an inflation balloon that is attached to and in fluid communication with a first inflation catheter, and the inflatable plunger deflated and in fluid communication with a second inflation catheter, the method comprising the steps of: introducing a guidewire into an accessing vessel to beyond an implantation site; inserting the first inflation catheter into a first lumen of a catheter sheath such that the cage is disposed proximate a distal end of the catheter sheath; threading the first inflation catheter over the guidewire via a guidewire lumen disposed through the first inflation catheter; advancing the catheter sheath into the accessing vessel until the cage is disposed at the implantation site; withdrawing the guidewire from the accessing vessel via the guidewire lumen; advancing the second inflation catheter through the guidewire lumen until the inflatable plunger in the delivery state is disposed within the cage; translating the catheter sheath proximally relative to the first inflation catheter until the cage is free from being contained within the first lumen; inflating the inflation balloon to expand the cage; deflating the inflation balloon; removing the thus deflated inflation balloon from the cage; inflating the inflatable plunger to the expanded configuration with fluid via the second inflation catheter; detaching the second inflation catheter from the inflatable plunger thus inflated to the expanded configuration; removing the first and second inflation catheters and the catheter sheath from the accessing vessel.

In further embodiments, a method for deployment of a transluminal cardiac valve, the cardiac valve including an operational state comprising a generally tubular cage disposed in an expanded configuration having a generally uniform central region, first and second ends each diametrically constricted relative to the central region, and a blood impervious region extending from the first end of the cage to within the generally uniform central region, and an inflatable plunger freely disposed and captured within the cage when inflated, and a delivery state including the generally tubular cage disposed in a collapsed configuration and crimped onto an inflation balloon that is attached to and in fluid communication with a first inflation catheter, and the inflatable plunger deflated and in fluid communication with a second inflation catheter, the method comprising the steps of: introducing a guidewire into an accessing vessel to beyond an implantation site; inserting the first inflation catheter into a first lumen of a catheter sheath such that the cage is disposed proximate a distal end of the catheter sheath; inserting the second inflation catheter into a second lumen of the catheter sheath such that the inflatable plunger is disposed proximate the distal end of the catheter sheath; threading the catheter sheath over the guidewire via a guidewire lumen disposed through at least a portion of the catheter sheath; advancing the catheter sheath into the accessing vessel until the cage is disposed at the implantation site; withdrawing the guidewire from the accessing vessel via the guidewire lumen; ntranslating the catheter sheath proximally relative to the first inflation catheter until the cage is free from being contained within the first lumen; inflating the inflation balloon to expand the cage; deflating the inflation balloon; withdrawing the first inflation catheter back into the first lumen; advancing the second inflation catheter distally until the inflatable plunger is within the cage; inflating the inflatable plunger to the expanded configuration; detaching the second inflation catheter from the inflatable plunger thus inflated to the expanded configuration; removing the first and second inflation catheters and the catheter sheath from the accessing vessel.

What is claimed is:
1. A transluminal cardiac valve, comprising:
  an expandable generally tubular cage including when expanded:
    a generally uniform central region;
    first and second ends each diametrically constricted relative to the central region, wherein the first end and the second end each further comprise an opening along the end in fluid communication with the generally uniform central region;

a first frustoconical transitional portion between the first end and the central region, and a second frustoconical transitional portion between the second end and the central region; and a blood impervious region extending from the first end of the cage to within the generally uniform central region; and an inflatable plunger freely disposed and captured within the cage when inflated.

2. The transluminal cardiac valve of claim 1, wherein the generally tubular cage comprises a plurality of struts forming cells therebetween when the cage is expanded.

3. The transluminal cardiac valve of claim 2, wherein the cells within the blood impervious region are filled by a blood impervious material.

4. The transluminal cardiac valve of claim 3, wherein the blood impervious material comprises a polymeric material.

5. The transluminal cardiac valve of claim 3, wherein the blood impervious material is selected from a group of blood impervious materials consisting of: porous woven metal mesh and porous non-woven metal film.

6. The transluminal cardiac valve of claim 1, wherein the inflatable plunger is made from a material selected from a group of materials consisting of: a vacuum deposited layer of metal, multiple vacuum deposited layers of metal, a polymeric material, and a pseudometallic material.

7. The transluminal cardiac valve of claim 1, wherein the inflatable plunger is inflated with an inflation medium selected from a group of inflation media consisting of: a gas, a liquid, and a hardening polymeric material.

8. The transluminal cardiac valve of claim 1, wherein the expandable generally tubular cage is balloon-expandable.

9. The transluminal cardiac valve of claim 1, wherein the expandable generally tubular cage is self-expanding.

10. The transluminal cardiac valve of claim 1, wherein the expandable generally tubular cage is manufactured from a pseudometallic material.

11. A transluminal cardiac valve, comprising:
    an operational state including:
        a generally tubular cage disposed in an expanded configuration having:
            a generally uniform central region;
            first and second ends each diametrically constricted relative to the central region, wherein the first end and the second end each further comprise an opening along the end in fluid communication with the generally uniform central region;
            a first frustoconical transitional portion between the first end and the central region, and a second frustoconical transitional portion between the second end and the central region; and
            a blood impervious region extending from the first end of the cage to within the generally uniform central region; and
        an inflatable plunger freely disposed and captured within the cage when inflated; and
    a delivery state including:
        the generally tubular cage disposed in a collapsed configuration and crimped onto an inflation balloon that is attached to and in fluid communication with an inflation catheter.

12. The transluminal cardiac valve of claim 11, wherein the delivery state further includes the inflatable plunger deflated and in fluid communication with a second inflation catheter.

13. The transluminal cardiac valve of claim 11, further including a catheter sheath having an outer diameter of about 12 French, wherein the generally tubular cage disposed in the collapsed configuration is adapted to be contained in the collapsed configuration within a lumen of the catheter sheath.

14. The transluminal cardiac valve of claim 11, wherein the generally tubular cage is made from one or more layers of vacuum deposited metal.

15. The transluminal cardiac valve of claim 14, wherein the vacuum deposited metal includes controlled heterogeneities along a luminal surface of the central region.

16. The transluminal cardiac valve of claim 14, wherein the vacuum deposited metal comprises nitinol.

17. A method for deployment of a transluminal cardiac valve, the cardiac valve including an operational state comprising a generally tubular cage disposed in an expanded configuration having a generally uniform central region, first and second ends each diametrically constricted relative to the central region, wherein the first end and the second end each further comprise an opening along the end in fluid communication with the generally uniform central region, a first frustoconical transitional portion between the first end and the central region, and a second frustoconical transitional portion between the second end and the central region, and a blood impervious region extending from the first end of the cage to within the generally uniform central region, and an inflatable plunger freely disposed and captured within the cage when inflated, and a delivery state including the generally tubular cage disposed in a collapsed configuration and crimped onto an inflation balloon that is attached to and in fluid communication with a first inflation catheter, and the inflatable plunger deflated and in fluid communication with a second inflation catheter, the method comprising the steps of:
    inserting the generally tubular cage in the delivery state into a lumen of a catheter sheath such that the cage is disposed proximate a distal end of the catheter sheath;
    advancing the catheter sheath into a patient until the cage is disposed at an implantation site;
    translating the catheter sheath proximally relative to the first inflation catheter until the cage is free from being contained within the lumen;
    inflating the inflation balloon to expand the cage;
    deflating the inflation balloon;
    removing the thus deflated inflation balloon and the first inflation catheter from the lumen;
    inserting the inflatable plunger in the delivery state such that the inflatable plunger is disposed within the cage;
    inflating the inflatable plunger to the expanded configuration with fluid via the second inflation catheter;
    detaching the second inflation catheter from the inflatable plunger thus inflated to the expanded configuration;
    removing the second inflation catheter and the catheter sheath from the patient.

18. The method of claim 17, wherein the step of inflating the inflation balloon to expand the cage further comprises the step of inflating the inflation balloon to expand the cage for post deployment dilatation of the cage to achieve adequate setting of the cage at the implantation site, and further including the following step before the step of inflating the inflation balloon:
    allowing the cage to self-expand at the implantation site.

19. The method of claim 17, further including the following step before the step of translating the catheter sheath proximally relative to the first inflation catheter until the cage is free from being contained within the lumen:
    minimizing motion at the implantation site.

20. The method of claim 17, wherein the implantation site is selected from a group of implantation sites consisting of: an anatomical site of a damaged cardiac valve and within the descending thoracic aorta.

* * * * *